US010987523B2

(12) United States Patent
Sheng et al.

(10) Patent No.: US 10,987,523 B2
(45) Date of Patent: Apr. 27, 2021

(54) PLATFORM FOR INTENSITY MODULATED RADIATION THERAPY

(71) Applicant: The Regents of the University of California, Oakland, CA (US)

(72) Inventors: Ke Sheng, Los Angeles, CA (US); Dan Nguyen, Los Angeles, CA (US); Dan Ruan, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/770,489

(22) PCT Filed: Oct. 21, 2016

(86) PCT No.: PCT/US2016/058053
§ 371 (c)(1),
(2) Date: Apr. 23, 2018

(87) PCT Pub. No.: WO2017/070433
PCT Pub. Date: Apr. 27, 2017

(65) Prior Publication Data
US 2019/0054316 A1 Feb. 21, 2019

Related U.S. Application Data

(60) Provisional application No. 62/245,840, filed on Oct. 23, 2015.

(51) Int. Cl.
*A61N 5/10* (2006.01)
(52) U.S. Cl.
CPC ......... *A61N 5/1045* (2013.01); *A61N 5/1036* (2013.01); *A61N 5/1077* (2013.01); *A61N 2005/1092* (2013.01)

(58) Field of Classification Search
CPC .......... A61N 5/00; A61N 5/10; A61N 5/1045; A61N 5/1077; A61N 5/1036; A61N 5/103;
(Continued)

(56) References Cited

U.S. PATENT DOCUMENTS 6,526,123 B2 *  2/2003  Ein-Gal ............... A61N 5/1042
                                                         250/505.1
6,600,810 B1 *  7/2003  Hughes .................... G21K 1/04
                                                         378/147
(Continued)

FOREIGN PATENT DOCUMENTS

| WO | 1996041349 | 12/1996 |
| WO | 2001027939 | 4/2001 |
| WO | 2014133849 | 9/2014 |

OTHER PUBLICATIONS

Chambolle, A. et al. "A first-order primal-dual algorithm for convex problems with applications to imaging." Journal of mathematical imaging and vision 40.1 (2011): 120-145.
(Continued)

*Primary Examiner* — Jurie Yun
(74) *Attorney, Agent, or Firm* — Quarles & Brady LLP

(57) ABSTRACT

In certain embodiments novel sparse orthogonal collimators (SOCs) for use in radiotherapy are provided. In certain embodiments the SOCs comprise 2 layer 4 bank orthogonal collimators with 2-8 leaves in each of the 4 banks. Instead of using the limited heuristic approach to create jaw-only IMRT, a novel fluence map optimization method is provided based on wavelet decomposition and this method is used for IMRT. An algorithm to simplify the fluence maps with minimal and predictable dose quality compromise is also provided.

7 Claims, 17 Drawing Sheets

(58) Field of Classification Search
CPC .. A61N 5/1031; A61N 5/1047; A61N 5/1071; A61N 2005/1092; A61B 6/06; G21K 1/00; G21K 1/02; G21K 1/04
USPC .......... 378/65, 147, 149, 150, 151, 152
See application file for complete search history.

(56) References Cited

U.S. PATENT DOCUMENTS

| | | | |
|---|---|---|---|
| 7,095,823 B2 | 8/2006 | Topolnjak et al. | |
| 7,583,775 B2* | 9/2009 | Ozaki | G21K 1/04 250/370.11 |
| 2014/0239204 A1 | 8/2014 | Orton et al. | |
| 2015/0170778 A1 | 6/2015 | Echner et al. | |
| 2015/0273239 A1 | 10/2015 | Hsu et al. | |
| 2018/0043183 A1 | 2/2018 | Sheng et al. | |

OTHER PUBLICATIONS

Chang, Sha X., et al. "Compensators: an alternative IMRT delivery technique." Journal of Applied Clinical Medical Physics 5.3 (2004): 15-36.

Condat, L.. "A primal-dual splitting method for convex optimization involving Lipschitzian, proximable and linear composite terms." Journal of Optimization Theory and Applications 158.2 (2013): 460-479.

Dai, J.-R., et al. "Intensity-modulation radiotherapy using independent collimators: An algorithm study." Medical physics 26.12 (1999): 2562-2570.

Dong, P., et al. "4p non-coplanar liver SBRT: a novel delivery technique." International Journal of Radiation Oncology* Biology* Physics 85.5 (2013): 1360-1366.

Dong, P., et al. "4p noncoplanar stereotactic body radiation therapy for centrally located or larger lung tumors." International Journal of Radiation Oncology* Biology* Physics 86.3 (2013): 407-413.

Dong, P., et al. "Feasibility of prostate robotic radiation therapy on conventional C-arm linacs." Practical radiation oncology 4.4 (2014): 254-260.

Dong, P., et al. "Feasibility of using intermediate x-ray energies for highly conformal extracranial radiotherapy." Medical physics 41.4 (2014).

Earl, M. A., et al. "Jaws-only IMRT using direct aperture optimization." Medical physics 34.1 (2007): 307-314.

Xia, P. et al. "Multileaf collimator leaf sequencing algorithm for intensity modulated beams with multiple static segments." Medical Physics 25.8 (1998): 1424-1434.

Grégoire, V., et al. "State of the art on dose prescription, reporting and recording in intensity-modulated radiation therapy (ICRU report No. 83)." Cancer/Radiothérapie15.6-7 (2011): 555-559.

International Search Report and Written Opinion for PCT/US2016/058053, dated Feb. 1, 2017, 10 pages.

Kim, Y. et al. "A feasibility study of using conventional jaws to deliver IMRT plans in the treatment of prostate cancer." Physics in Medicine & Biology52.8 (2007): 2147.

Mu, G., and P. Xia. "A feasibility study of using conventional jaws to deliver complex IMRT plans for head and neck cancer." Physics in Medicine & Biology 54.18 (2009): 5613.

Nangia, S., et al. "Compensator-based intensity-modulated radiotherapy in head and neck cancer: our experience in achieving dosimetric parameters and their clinical correlation." Clinical Oncology 18.6 (2006): 485-492.

Nguyen, D., et al. "Dose domain regularization of MLC leaf patterns for highly complex IMRT plans." Medical physics 42.4 (2015): 1858-1870.

Robinson, J., et al. "Evaluating dosimetric accuracy of flattening filter free compensator-based IMRT: measurements with diode arrays." Medical physics 39.1 (2012): 342-352.

Romeijn, H. E., et al. "A colomn generation approach to radiation therapy treatment planning using aperture modulation." SIAM Journal on Optimization 15.3 (2005): 838-862.

Romeijn, H. E., et al. "A novel linear programming approach to fluence map optimization for intensity modulated radiation therapy treatment planning." Physics in Medicine & Biology 48.21 (2003): 3521.

Tajima, Y., et al. "Dosimetric evaluation of compensator intensity modulation-based stereotactic body radiotherapy fo Stage I non-small-cell lung cancer." The British journal of radiology 88.1052 (2015): 20150122.

Waghorn, B. J., et al. "A comparison of the dosimetric effects of intrafraction motion on step-and-shoot, compensator, and helical tomotherapy-based IMRT." Journal of applied clinical medical physics 14.3 (2013): 4210-4210.

Webb, S., et al. "Intensity-modulated radiation therapy (IMRT) by a dynamic-jaws-only (DJO) technique in rotate-translate mode." Physics in Medicine & Biology 55.21 (2010): N495.

Webb, S.. "Intensity-modulated radiation therapy using only jaws and a mask." Physics in Medicine & Biology 47.2 (2002): 257.

* cited by examiner

Classical Haar Transform $$H_c^T \quad \alpha_c \quad H_c \quad =$$

Modified Transform $$H_m^T \quad \alpha_m \quad H_m \quad =$$

PLATFORM FOR INTENSITY MODULATED RADIATION THERAPY

CROSS-REFERENCE TO RELATED APPLICATIONS

This application represents the national stage entry of International Application PCT/US2016/058053, filed Oct. 21, 2016, which claims benefit of and priority to U.S. Provisional Patent Application 62/245,840, filed on Oct. 23, 2015, which is incorporated herein by reference in its entirety for all purposes.

STATEMENT OF GOVERNMENTAL SUPPORT

This invention was made with government support under Grant No. NIH R43CA183390 awarded by the National Institutes of Health. The Government has certain rights in this invention.

BACKGROUND

Intensity modulated radiation therapy (IMRT) is a cornerstone of modern radiation therapy physics. By modulating the incident X-ray intensities, IMRT has provided unprecedented control over X-ray dose distributions to target tumors and spare normal tissues. IMRT was afforded by the development of inverse optimization algorithms and enabling hardware. With a few exceptions, such as the compensator based IMRT (Chang et al. (2004) *J. Appl. Clin. Med. Phys.* 5(3): 15-36; Tajima et al. (2015) *Br. J. Radiol.* 88(1052): 20150122; Waghorn et al. (2013) *J. Appl. Clin. Med. Phys.* 14(3): 4210; Robinson et al. (2012) *Med. Phys.* 39(1): 342-352; Nangia et al. (2006) *Clin. Oncol. (R. Coll. Radiol.)*, 18(6): 485-492), the multileaf collimator (MLC) that consists of a large number of thin moving tungsten leaves has been the dedicated device to modulate the X-ray fluence.

Due to considerations including the mechanical complexity, cost, accessibility and reliability of early MLCs, attempts have been made to use only the orthogonal jaws on conventional linacs for IMRT (Mu and Xia (2009) *Phys. Med. Biol.* 54(18): 5613-5623; Earl et al. (2007) *Med. Phys.* 34(1): 307-314; Webb (2002) *Phys. Med. Biol.* 47(2): 257-275). Jaws-only IMRT requires the entire IMRT plan to be delivered using exclusively rectangular apertures. Different methods have been used to generate these apertures, including fluence stripping (Dai and Hu (1999) *Med. Phys.*, 26(12): 2562-2570) and direct aperture optimization (DAO) (Earl et al. (2007) *Med. Phys.* 34(1): 307-314). In the former method, a fluence optimization was first performed and the resulting fluence was subsequently stripped to rectangles for jaws-only delivery. The method inevitably suffered from dosimetric quality compromise and low delivery efficiency due to sequential simplification of the fluence maps. To address these difficulties, additional collimator devices such as masks (Webb (2002) *Phys. Med. Biol.* 47(2): 257-275) and rotational and dynamic jaws (Webb and Poludniowski (2010) *Phys. Med. Biol.* 55(21): N495-506) have been theorized but not implemented.

The direct aperture optimization (DAO) approach has been incorporated into a commercial planning system (Earl et al. (2007) *Med. Phys.* 34(1): 307-314). This approach utilizes a simulated annealing process to search and select rectangular apertures that minimized an objective function. It was shown that for simple cases, the jaws-only IMRT can achieve superior plan quality to 3D conformal plans (Kim et al. (2007) *Phys. Med. Biol.*, 52(8): 2147-2156). In a follow up study, Mu and Xia showed that even for more complex head and neck IMRT plans, the jaws-only approach can result in acceptable dosimetry, at a cost of longer delivery time (Mu and Xia (2009) *Phys. Med. Biol.* 54(18): 5613-5623).

With the maturation of MLC technology, the problems that plagued early IMRT delivery, such as reliability and cost, have been partially mitigated. To the best of our knowledge, the jaws-only IMRT has not been clinically adopted due to limitations in its dosimetric quality and delivery efficiency.

SUMMARY

To deliver high quality intensity modulated radiotherapy (IMRT) using a novel generalized sparse orthogonal collimators (SOC), a novel direct aperture optimization (DAO) approach based on discrete Haar wavelet representation was introduced. In various embodiments the formulation of the inverse optimization problem that consists of an L2 fidelity term and an L1 regularization term (Nguyen et al. (2015) *Med. Phys.*, 42(4): 1858-1870). The solution algorithm based on the first-order primal-dual approach gives remarkable freedom to modify and simplify the optimized fluence maps. Because the optimization was performed in the dose domain, substantial modification and simplification of the fluence maps is possible without degrading the dosimetric quality. This development paves the path to a new algorithm that optimally the use of s sparse orthogonal collimator as described herein.

A total of 7 patients-2 GBM, 3 head & neck (including 1 with 3 prescription doses) and 2 lung were included. Twenty non-coplanar beams were selected using a column generation and pricing optimization method. The SOC is a generalized conventional orthogonal collimator with N leaves in each collimator bank, where N=1, 2, or 4. SOC degenerates to conventional jaws when N=1. For SOC-based IMRT, Haar-based fluence optimization (HFO) was performed to optimize the fluence maps in the Haar wavelet domain, producing fluence maps that can be directly converted into a set of deliverable rectangular apertures. In order to optimize the dose distribution and minimize the number of apertures used, the overall objective was formulated to incorporate an L2 penalty reflecting the difference between the prescription and the projected doses, and an L1 sparsity regularization term to encourage a low number of non-zero Haar wavelet coefficients. The optimization problem was solved using the Chambolle-Pock algorithm, a first-order primal-dual algorithm. Performance of HFO was compared to conventional two-step IMRT optimization including fluence map optimization and Direct stratification for MLC Segmentation (DMS) using the same number of segments. For the HFO plans, segment travel time for SOC delivery was evaluated for the N=1, N=2, and N=4 SOC designs to characterize the improvement in delivery efficiency as a function of N.

Comparable PTV dose homogeneity and coverage were observed between the HFO and the DMS plans. The HFO plans were slightly superior to the MLC based DMS plans in sparing critical structures. On average, the maximum and mean critical organ doses were reduced by 2.27% and 1.38% of the prescription dose. The average number of delivery segments was 16.39 segments per beam for both the HFO and DMS plans. The N=2 and N=4 SOC designs were, on average, 1.78 and 2.18 times more efficient than the N=1 SOC design to deliver. The mean aperture size produced by the HFO plans was 4.4 times larger than that of the DMS plans. The DAO and dose domain optimization approach enabled high quality IMRT plans using a low-complexity collimator setup. The dosimetric quality is comparable or slightly superior to conventional MLC-based IMRT plans using the same number of delivery segments. The SOC IMRT delivery efficiency can be significantly improved by increasing the leaf numbers, but the number is still significantly lower than the number of leaves in a typical MLC.

Accordingly, in certain embodiments, sparse orthogonal collimators and methods of optimizing fluence maps for use there with are provided.

Various embodiments contemplated herein may include, but need not be limited to, one or more of the following:

Embodiment 1

A sparse orthogonal collimator for shaping a radiotherapy beam, said collimator comprising first bank of individually longitudinally movable elongate leaves, and a second bank of individually longitudinally movable elongate leaves the second bank being disposed in an opposed relationship to the first bank; third bank of individually longitudinally movable elongate leaves, and a fourth bank of individually longitudinally movable elongate leaves the fourth bank being disposed in an opposed relationship to said third bank; and said first bank and said second bank being oriented orthogonal to said third bank and fourth bank; and said first bank, second bank, third bank, and fourth bank each individually contain from two to four leaves.

Embodiment 2

The collimator of embodiment 1, wherein all of the leaves comprising said first bank and said second bank form a first layer in said collimator and all the leaves comprising said third bank and said fourth bank form a second layer disposed beneath said first layer.

Embodiment 3

The collimator of embodiment 1, wherein: a first subset of the leaves comprising said first bank and said second bank are disposed in a first layer in said collimator and a second subset of the leaves comprising said first bank and said second bank are disposed in a second layer in said collimator; a first subset of the leaves comprising said third bank and said fourth bank are disposed in said first layer in said collimator and a second subset of the leaves comprising said third bank and said fourth bank are disposed in said second layer in said collimator; and the first subset of the leaves comprising said first bank and said second bank are disposed in said first layer so that they do not collide with the first subset of leaves comprising said third bank and said fourth bank disposed in said first layer; and the second subset of the leaves comprising said first bank and said second bank are disposed in said second layer so that they do not collide with the second subset of leaves comprising said third bank and said fourth bank disposed in said second layer.

Embodiment 4

The collimator according to any one of embodiments 1-3, wherein the total number of leaves is a power of 2.

Embodiment 5

The collimator according to any one of embodiments 1-4, wherein said first bank said second bank said third bank and said fourth bank each contain the same number of leaves.

Embodiment 6

The collimator according to any one of embodiments 1-5, wherein said collimator contains 4, 8, 16, or 32 leaves.

Embodiment 7

The collimator according to any one of embodiments 1-6, wherein each bank contains 2, 4, or 8 leaves.

Embodiment 8

The collimator of embodiment 7, wherein each bank contains 4 leaves.

Embodiment 9

The collimator according to any one of embodiments 1-8, wherein the width of leaves comprising said collimator ranges from about 2.5 mm up to about 5 cm.

Embodiment 10

The collimator of embodiment 9, wherein leaves comprising said collimator have a width of about 0.5 cm, or about 1 cm, or about 1.5 cm, or about 2 cm, or about 2.5 cm, or about 3 cm, or about 3.5 cm, or about 4 cm, or about 4.5 cm, or about 5 cm.

Embodiment 11

The collimator of embodiment 9, wherein leaves comprising said collimator have a width of 1 cm.

Embodiment 12

The collimator of embodiment 11, wherein leaves comprising said collimator have a width of 2.5 cm.

Embodiment 13

The collimator of embodiment 11, wherein leaves comprising said collimator have a width of 2.5 mm.

Embodiment 14

The collimator according to any one of embodiments 1-13, wherein the leaves comprising said collimator are all the same width.

Embodiment 15

The collimator according to any one of embodiments 1-13, wherein said collimator produces a physical field size at the collimator ranging up to about 10 cm×10 cm.

Embodiment 16

The collimator according to any one of embodiments 1-13, and 15, wherein said collimator produces a maximum field size at treatment depth of about 20 cm×20 cm.

Embodiment 17

The collimator according to any one of embodiments 1-11, wherein said collimator produces a maximum field size up to about 2 cm×2 cm at the treatment depth.

Embodiment 18

The collimator according to any one of embodiments 1-17, wherein said collimator produces a minimum field size of about 1 mm×1 mm at the treatment depth.

Embodiment 19

The collimator according to any one of embodiments 1-18, wherein the thickness of leaves comprising said collimator ranges from about 1 cm to about 6 cm.

Embodiment 20

The collimator of embodiment 19, wherein the thickness of leaves comprising said collimator is about 1 cm, or about 1.5 cm, or about 2 cm, or about 2.5 cm, or about 3 cm, or about 3.5 cm, or about 4 cm, or about 4.5 cm, or about 5 cm, or about 5.5 cm, or about 6 cm.

Embodiment 21

The collimator according to any one of embodiments 1-20, wherein the length of leaves comprising said collimator ranges from about 2 cm up to about 15 cm.

Embodiment 22

The collimator according to any one of embodiments 1-20, wherein the length of leaves comprising said collimator is about 2 cm, or about 3 cm, or about 4 cm, or about 5 cm, or about 6 cm, or about 7 cm, or about 8 cm, or about 9 cm, or about 10 cm, or about 11 cm, or about 12 cm, or about 13 cm, or about 14 cm, or about 15 cm.

Embodiment 23

The collimator according to any one of embodiments 1-22, wherein leaves comprising said collimator includes a material selected from the group consisting of brass or brass alloy (for kV X-rays), and tungsten or tungsten alloy (for MV X-rays), 24: The collimator according to any one of embodiments 1-23, wherein each leaf in said collimator is operably coupled to a drive mechanism that provides longitudinal movement of the coupled leaf independent of the longitudinal movement of the other leaves comprising said collimator.

Embodiment 25

The collimator according to any one of embodiments 1-24, wherein said drive mechanism includes mechanism selected from the group consisting of a stepping motor, a magnetic actuator, and a pressure actuator.

Embodiment 26

The collimator of embodiment 25, wherein said drive mechanism includes a stepping motor.

Embodiment 27

The collimator of embodiment 26, wherein said stepping motor provides a step having a resolution as low as 1 µm.

Embodiment 28

The collimator according to any one of embodiments 24-27, wherein said drive mechanism provides a leaf position adjustable to an accuracy of at least at least ±0.1 mm.

Embodiment 29

The collimator according to any one of embodiments 1-28, wherein each leaf comprising said collimator is operably coupled to a position encoder.

Embodiment 30

The collimator of embodiment 29, wherein said position encoder includes a position encoder selected from the group consisting of a laser encoder, an optical encoder, and a magnetic encoder.

Embodiment 31

The collimator according to any one of embodiments 1-30, wherein said collimator is coupled to a controller that determines and adjusts the positions of the leaves comprising said collimator.

Embodiment 32

The collimator of embodiment 31, wherein said controller is configured to determine and adjust the positions of the leaves comprising said collimator during a radiotherapy treatment.

Embodiment 33

The collimator according to any one of embodiments 1-32, wherein said collimator is configured as a component of a linac and disposed to control the field size and shape of radiation emitted from said linac.

Embodiment 34

A system for collimating a therapeutic radiation beam, the system comprising: a sparse orthogonal collimator according to any one of embodiments 1-32; a radiotherapy device comprising said sparse orthogonal collimator disposed to control the field size and shape of emitted radiation; and a controller configured to adjust the position of the leaves comprising said sparse orthogonal collimator.

Embodiment 35

The system of embodiment 34, wherein said radiotherapy device produces electron or photon beams.

Embodiment 36

The system of embodiment 34, wherein said radiotherapy device produces electron, neutron, proton, x-ray, or gamma radiation.

Embodiment 37

The system of embodiment 34, wherein said radiotherapy device includes a linear accelerator (linac) configured to provide X-rays.

Embodiment 38

The system according to any one of embodiments 34-37, wherein said radiotherapy device is configured to operate in a coplanar beam orientation.

Embodiment 39

The system according to any one of embodiments 34-37, wherein said radiotherapy device is configured to operate in a non-coplanar beam orientation.

Embodiment 40

A method of generating a radiation treatment plan using a radiotherapy device comprising a sparse orthogonal collimator according to any one of embodiments 1-33 and/or a system according to any one of embodiments 34-39, said method comprising:
  providing a fluence maps for said radiation plan; and generating using a computer a time sequence of sparse orthogonal collimator leaf settings from said fluence maps, wherein said generating includes:
    representing a desired fluence map using discrete Haar wavelet coefficients; and
    optimizing Haar fluence using a direct aperture regularization approach centered on the dose domain optimization wherein sparsity is used to limit total number of Haar coefficients and thus total number of apertures while maintaining dosimetric quality; and
  generating and writing instruction files to implement said time sequence of sparse orthogonal collimator leaf settings to a tangible medium that can be executed by a radiotherapy device.

Embodiment 41

The method of embodiment 40, wherein said representing a desired fluence map includes representing a fluence map, $f_{mat}$, using discrete Haar wavelet coefficients, $\alpha_c$, such that:

$$H_c^T \alpha_c H_c = f_{mat} \qquad (1)$$

where $H_c$ is the classical Haar transform matrix, but changing the differential Haar transform, $H_c$, to a scaling function, which is a modified Haar transform, $H_m$, that uses a coefficient set, $\alpha_m$ where for a $2^n \times 2^n$ fluence matrix, the coefficient matrix $\alpha_m$ has dimensions $(2^{n+1}-1) \times (2^{n+1}-1)$, and $H_m$ has dimension $(2^{n+1}-1) \times 2^n$.

Embodiment 42

The method according to any one of embodiments 40-41, wherein said optimizing comprises:

$$\text{minimize } \tfrac{1}{2}\|W(AH_v\alpha_v - d_0)\|_2^2 + \lambda\|\alpha_v\|_1$$

$$\text{subject to } \alpha_v \geq 0, \qquad (4)$$

where $\alpha_v = \text{vec}(\alpha_m)$ is the optimization variable; $H_v$ is the Haar transform matrix for the coefficient vector; $W$ is a weighting factor for the structures of interest; $A$ is the fluence to dose transformation matrix; and $d_0$ is the desired dose.

Embodiment 43

The method of embodiment 42, wherein $d_0$ is set to the prescription dose for the planning target volume (PTV) and zero for the organs at risk (OARs).

Embodiment 44

The according to any one of embodiments 42-43, wherein the fluence to dose transformation matrix is calculated using a convolution/superposition code using a 6 MV x-ray polyenergetic kernel.

Embodiment 45

The method according to any one of embodiments 42-44, wherein said optimization is solved utilizing the Chambolle-Pock algorithm.

Embodiment 46

The method according to any one of embodiments 40-45, wherein said method includes aperture constraints during the optimization stage rather than after the optimization.

Embodiment 47

The method according to any one of embodiments 40-46, wherein said writing instruction files includes writing one or more instruction files to a tangible medium selected from the group consisting of a magnetic medium, an optical medium, a PAL chip, and a static RAM chip.

Embodiment 48

The method of embodiment 47, wherein said writing instruction files includes writing one or more instruction files to a CD, a flash drive, a DVD, and a hard drive.

Embodiment 49

The method according to any one of embodiments 40-48, wherein said instruction files contain a treatment plan comprising sparse orthogonal collimator leaf positions and optionally one or more of the following: machine gantry and couch positions, beam intensities, imager positions at a given time or plan delivery point.

Embodiment 50

The method of embodiment 49, wherein said treatment plan includes couch positions and gantry angles for a non-coplanar beam treatment.

Embodiment 51

The method of embodiment 49, wherein said treatment plan includes couch positions and gantry angles for a coplanar beam treatment.

Embodiment 52

A radiation treatment planning system for preparing treatment planning information for carrying out radiation treatment, said radiation treatment planning system comprising: an input unit with which an operator inputs at least a prescription dose and a treatment volume; a computational unit configured to generate a radiation treatment plan using a radiotherapy device comprising a sparse orthogonal collimator according to any one of embodiments 1-33, and said computational unit determines apertures for said sparse orthogonal collimator, and optionally determines treatment beams, machine, and table paths; and a display unit that displays said radiation treatment plan.

Embodiment 53

The treatment planning system where said computational unit is configured to perform a method according to any one of embodiments 40-51.

Embodiment 54

The system according to any one of embodiments 52-53, wherein said system further includes a 3D scanning system.

Embodiment 55

The system according to any one of embodiments 52-54, wherein said computational unit is configured to receive a CAT scan from a CT scanner or a patient medical record.

Embodiment 56

The system according to any one of embodiments 52-55, wherein said system is configured to output a treatment plan into a patient medical record.

Embodiment 58

A method of performing intensity modulated radiotherapy (IMRT) on a subject, said method comprising: inputting into a radiotherapy device controller an instruction file generated using a method according to any one of embodiments 40-51, wherein said radiotherapy device includes a sparse orthogonal collimator according to any one of embodiments; and operating said radiotherapy device using the inputted instruction set to deliver a radiation at a plurality of different apertures to said subject.

Embodiment 59

The method of embodiment 58, wherein said radiotherapy device includes a linac.

Embodiment 60

The method according to any one of embodiments 58-59, wherein said subject includes a human.

Embodiment 61

The method according to any one of embodiments 58-59, wherein said subject includes non-human mammal.

Embodiment 62

The method of embodiment 61, wherein said non-human mammal includes a small mammal having a mass of less than about 10 kg, or less than about 5 kg, or less than about 2 kg.

BRIEF DESCRIPTION OF THE DRAWINGS

FIG. 3A shows a "front" view of the collimator. FIG. 3B illustrates a view of the collimator showing the leaves at different layers. FIG. 3C illustrates one two-leaf bank of a sparse orthogonal collimator.

Figure 1:
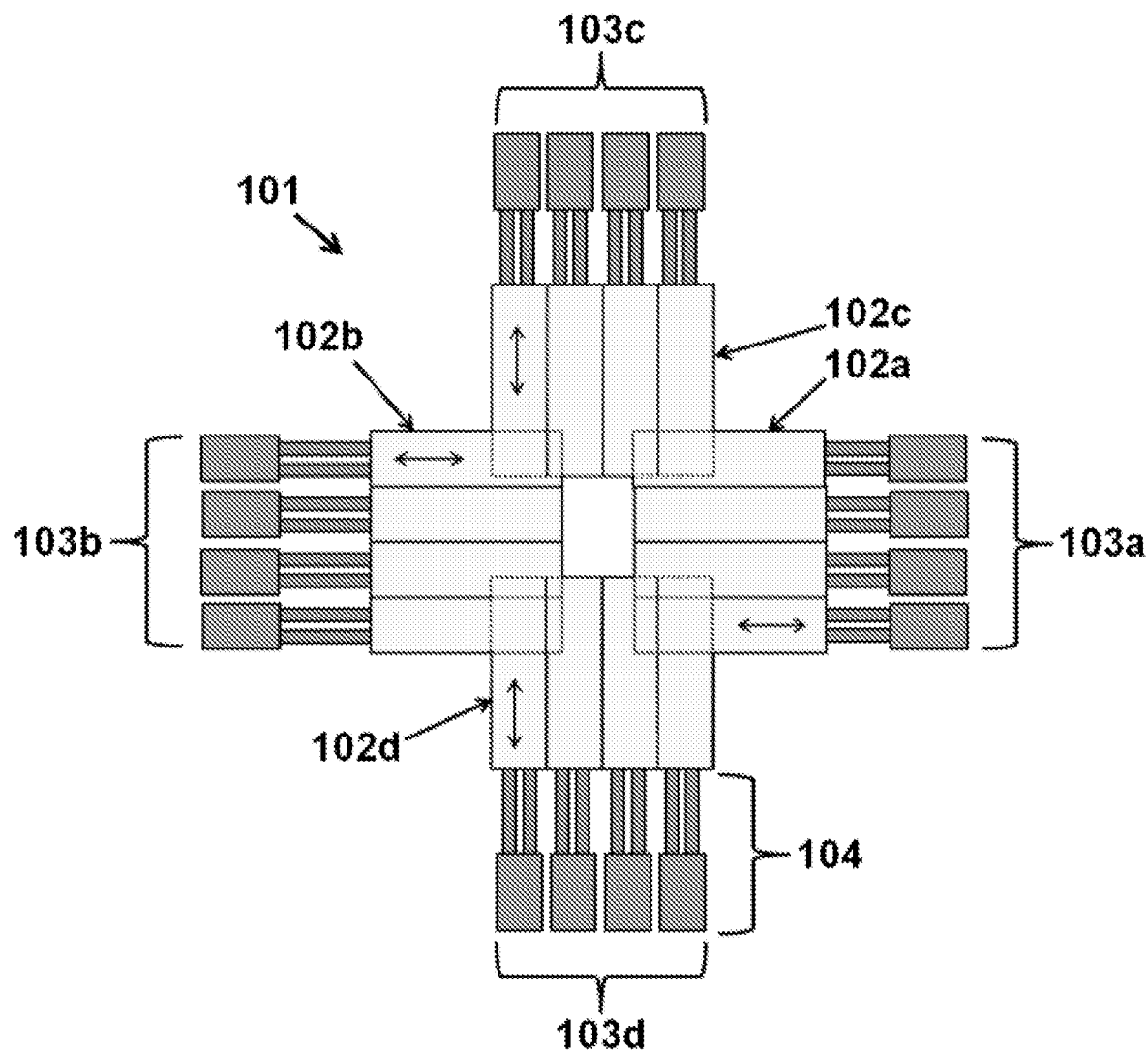
FIG. 1 schematically illustrates one embodiment of a sparse orthogonal collimator 101 comprising four banks of leaves 103a, 103b, 103c, and 103d where, as illustrated, each bank contains four leaves per bank and a first pair of opposed banks (103a, 103b) is disposed orthogonal to a second pair of opposed banks (103c, 103d).

$$\text{Efficiency} = \frac{1 \text{ leaf } SOC \text{ delivery time}}{x \text{ leaf } SOC \text{ delivery time}}.$$

DETAILED DESCRIPTION

Using radiation to treat cancer requires careful planning. Bombarding malignant tumors with high-energy X-rays can kill cancerous cells (or hinder their growth), but it is often impossible to deliver a terminal dose to the target without damaging nearby healthy organs in the process. Serious complications can occur when the surrounding healthy tissues receive too much of this collateral radiation. On the other hand, sacrificing a modest number of healthy cells may be tolerable since many organs are resilient enough to sustain a certain degree of damage while still providing their anatomical function and can eventually recover.

Therefore radiotherapy treatment plans seek methods of delivering a sufficient dose to the target (e.g., tumor), while carefully controlling the dose received by neighboring organs and other healthy tissues.

Intensity-modulated radiation therapy (IMRT) is a radiotherapy method that delivers higher doses to tumors and allows more precise conformation than the conventional 3D conformal radiotherapy. The primary delivery tool for IMRT is a linear accelerator that rotates on a gantry around the patient, emitting "modulated" beams of X-rays. This modulation has previously been accomplished by means of a device known as a multileaf collimator (MLC) which is attached to the accelerator. Its adjustable heavy-metal leaves act as a filter, blocking or allowing radiation through in a precise manner controlled by a computer, in order to tailor the beam shape to the shape of the tumor volume while minimizing exposure of the neighboring structures.

Several mathematical problems arise in order to optimally administer IMRT. Treatment proceeds by rotating the accelerator around the patient and coordinating the leaf movements in the MLC so that the radiation delivered conforms to some desirable dose distribution at each gantry (beam) angle. Part of determining a radiotherapy treatment involves determining the number and values of the gantry angles to be used in a particular treatment. Methods of determining gantry angles for co-planar and non-coplanar radiotherapy treatments are known to those of skill in the art (see, e.g., Dong et al. (2013) *Int. J. Radiat. Oncol. Biol. Phys.* 85: 1360-1366; Dong et al. (2013) *Int. J. Radiat. Oncol. Biol. Phys.* 86: 407-413). Additionally, improved radiotherapy methods utilizing the entire $4\pi$ solid angle are described in copending patent U.S. Provisional Patent Application No. 62/128,906, filed on Mar. 5, 2015, entitled RADIOTHERAPY UTILIZING THE ENTIRE 4PI SOLID ANGLE, which is incorporated herein by reference for the methods described therein. It is noted that typically, increasing the number of gantry angles will increase the quality, the time, and the cost of the treatment.

In addition to determining the beam angles, one must also determine how intense the beams should be at each point (x, y) on the aperture for all gantry angles. These intensity profiles, or fluence maps, have typically been represented by two-dimensional, nonnegative functions, e.g. $I_a(x, y)$ for $a=1, 2, \ldots, k$, where k is the number of gantry angles in use. The process of determining the functions $I_a(x, y)$ is often called fluence map optimization.

Once the fluence maps are determined, they are converted into collimator leaf sequences that attempt to realize them. The longer a collimator leaf is open at a certain position (x, y), the more dose the tissue along a straight path from that position (plus some surrounding tissue) absorbs. The process of converting fluence maps into the opening and closing movements of leaves is called leaf-sequencing.

The conventional MLC was intuitively designed as a finger like device by extending and retracting individual leaves, the radiation level of the areas under the leaf can be quantitatively controlled. Clearly, the thinner the leaves, the higher the resolution can be achieved. Currently, leaves as thin as 1 mm are used. However, making leaves this thin and moving them in and out with high accuracy and reproducibility has been a significant engineering challenge. It is very expensive and often forces a compromise between the field size and resolution. For example, the high resolution MLC option on Varian machines results in a specialized radiosurgery machine with small field size. Because of the challenges and cost, it has proven impossible to make a reliable MLC for applications such as small animal irradiators that are attempting to replicate human treatment so the experimental results are more meaningful.

To overcome these difficulty, a sparse orthogonal collimator (SOC) was designed and algorithm were determined to drive it. SOC consists of 2 layer 4 bank orthogonal collimators with 2-8 leaves in each of the 4 banks (see, e.g. FIGS. 1, 2, and 3A-3C).

Instead of using the limited heuristic approach to create jaw-only IMRT, we introduce a novel fluence map optimization method based on wavelet decomposition and use it for IMRT. We have developed an innovative algorithm to simplify the fluence maps with minimal and predictable dose quality compromise. We further used Haar wavelet decomposition to convert the simplified fluence maps to patches that can be achieved using the SOC while maintaining high dosimetric quality. Compared to the conventional multi-leaf collimator (MLC) using 120 leaved, a similar level of intensity modulation can be achieved using 32 or fewer leaves in SOC.

It is believed that SOC will be less expensive to make and maintain. It will achieve both high resolution and large field coverage. It is also feasible to make SOC for applications that are highly limited in space and provide higher resolution modulation such as small animal irradiation and for use with robotically mounted linacs.

Sparse Orthogonal Collimators.

In various embodiments, the sparse orthogonal collimators comprise two layer four bank orthogonal collimator with 2-8 leaves in each of the four banks. One embodiment of such a collimator is schematically in FIG. 1. The illustrated sparse orthogonal collimator 101 comprises four banks of leaves 103*a*, 103*b*, 103*c*, and 103*d* where, as illustrated, each bank contains four leaves 102*a*, 102*b*, 102*c*, and 102*d* respectively. As illustrated, banks 103*a* and 103*b* are disposed in an opposed relationship with each other and banks 103*c* and 103*d* are disposed in an opposed relationship with each other. The leaves comprising the banks are elongate and individually longitudinally moveable in the directions illustrated by the arrows on shown on the leaves. In the illustrated embodiment, all the leaves comprising opposed banks 103*a* and 103*b* are disposed in a first layer in the collimator, while all the leaves comprising opposed banks 103*c* and 103*d* are disposed in a second layer in the collimator, in this illustration, below the first layer. By using the two layers in this configuration, orthogonally oriented leaves will not collide.

Figure 2:
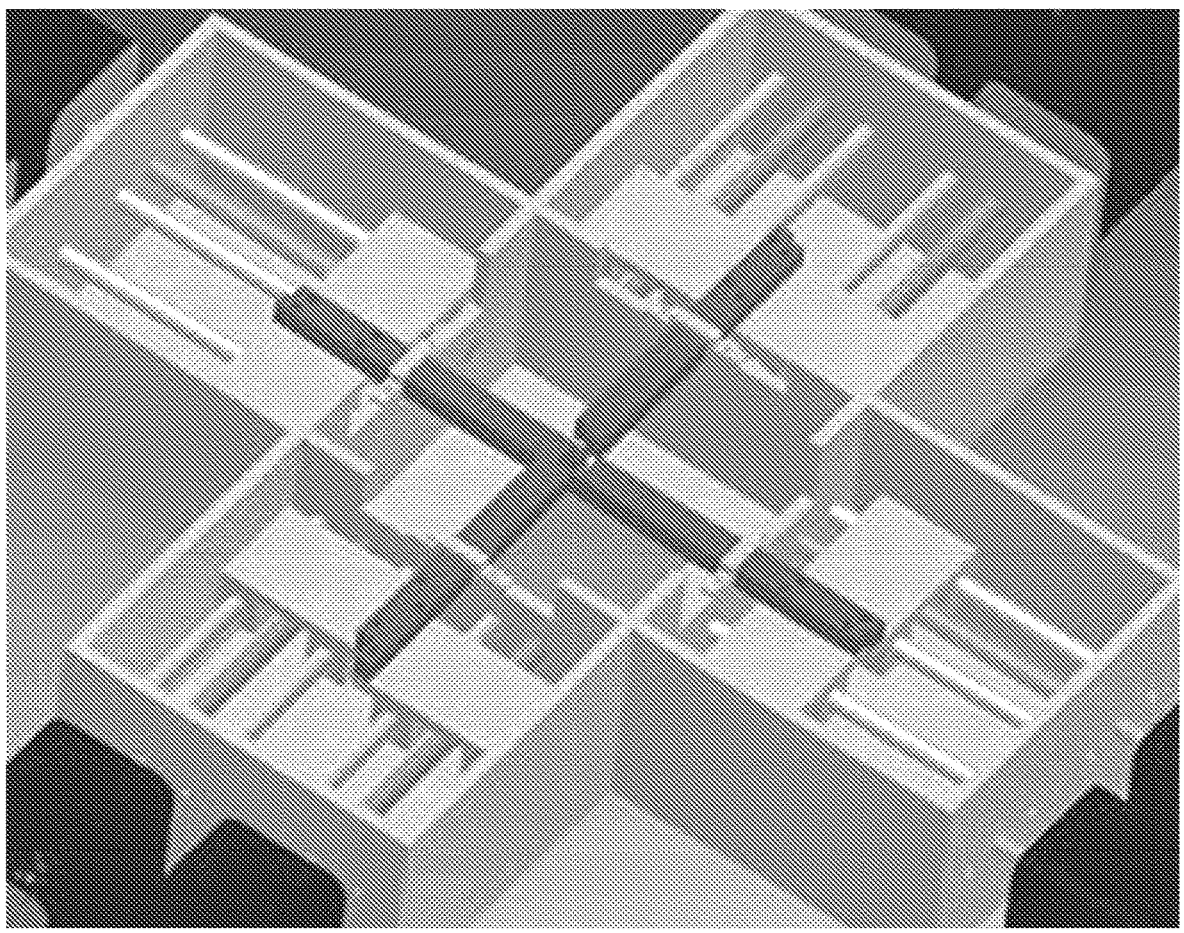
FIG. 2 illustrates one embodiment of a sparse orthogonal collimator comprising four banks of leaves where, as illustrated, each bank contains two leaves per bank.
Figure 3A:
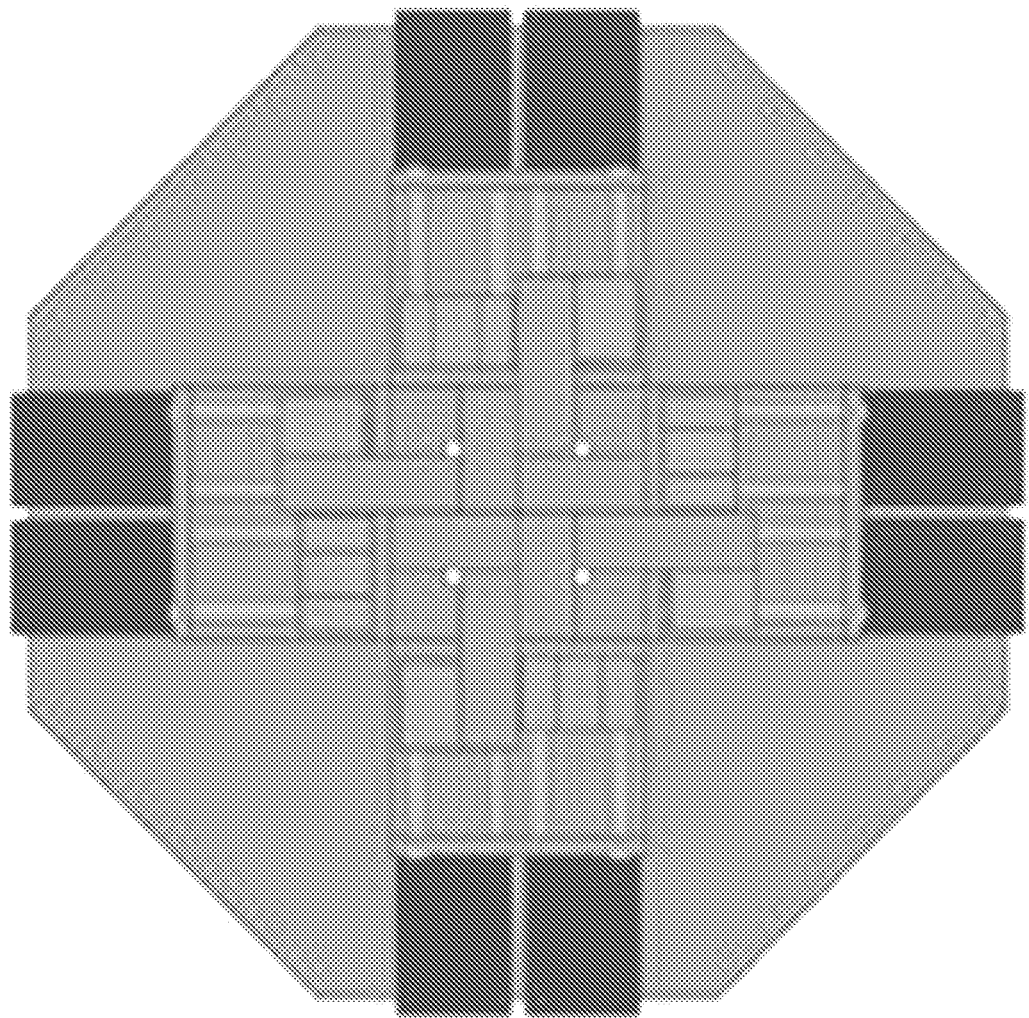
FIGS. 3A-3C illustrate one embodiment of a sparse orthogonal collimator comprising two leaves/bank where different leaves in a bank may be on different layers in the collimator.
Figure 3B:
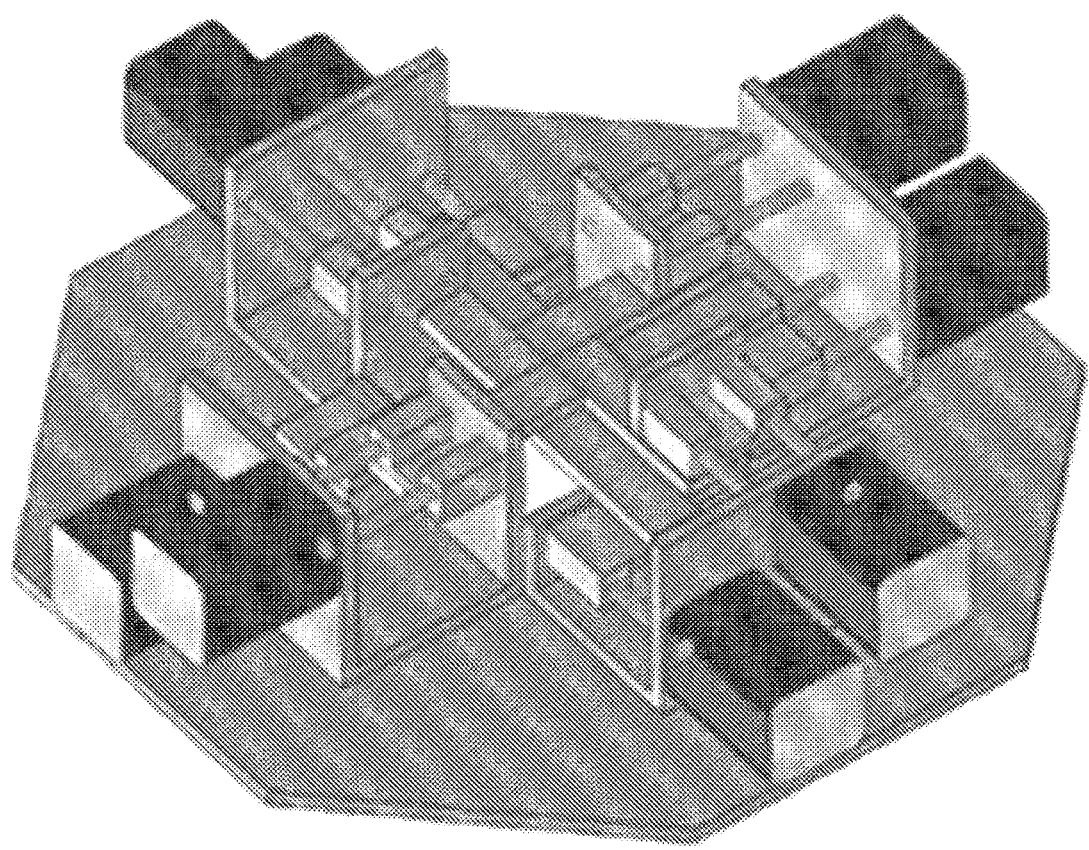

The collimator configuration shown in FIGS. 1 and 2 is illustrative, however, and not limiting. For example, in certain embodiments, different leaves comprising a single bank can be disposed in different layers in the collimator and can be configured so that orthogonally disposed leaves do not collide. One such example is shown in FIGS. 3A and 3B leaves. As shown in this illustrative embodiment, each bank contains two leaves, but the two leaves are at different layers in the collimator. The illustrated arrangement allows orthogonal leaves to extend without collision.

Typically, in various embodiments, the sparse orthogonal collimator will contain one or more drive mechanisms that control the position/movement of the leaves. In certain embodiments, drive mechanisms are provided that allow each leaf comprising the collimator to be individually moved/positioned.

Drive mechanisms that are suitable for use in the sparse orthogonal collimators (SOCs) described herein are known to those of skill in the art and often used in multi-leaf collimators (MLCs). Illustrative drive mechanisms include, but are not limited to mechanically positioning mechanism such as a lead screw or rack and pinion driven, e.g., by a motor (e.g., a stepping motor), a pneumatic positioning system (see, e.g., U.S. Patent Pub. No: 2015/0170778), an electromagnetic positioning system (see, e.g. U.S. Patent Pub. No: 2014/0239204), a combined linear induction motor and encoder, and the like.

Figure 3C:
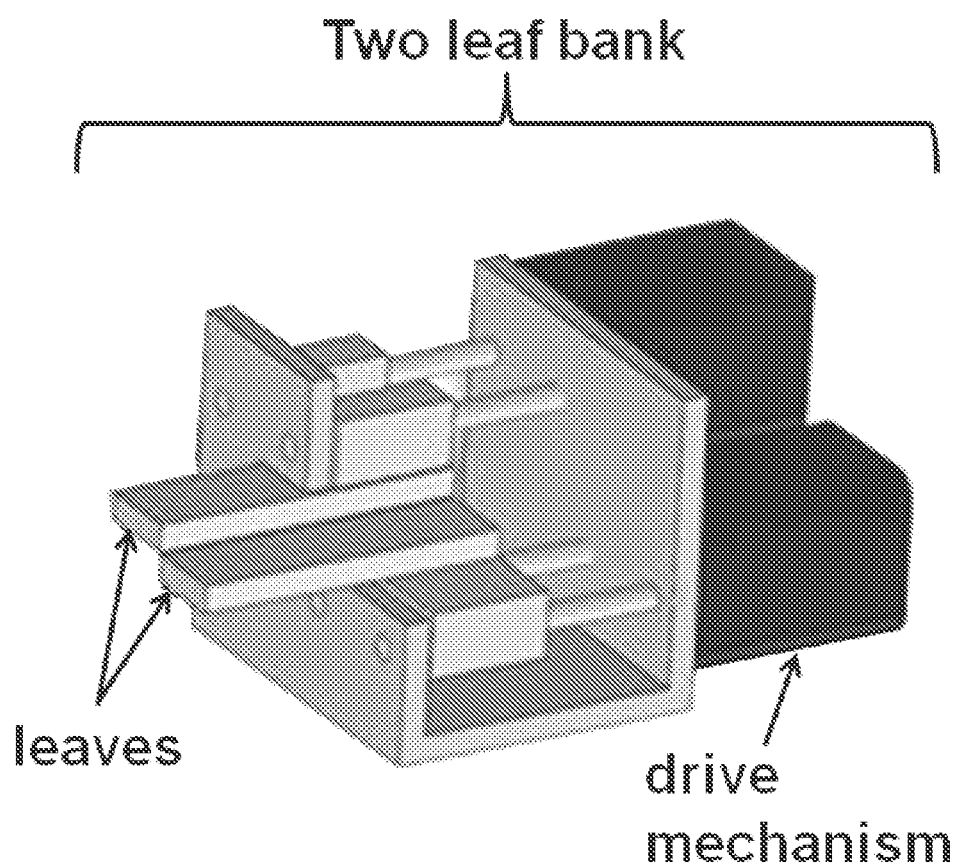

One illustrative drive mechanism (e.g., a stepper motor) 104 is shown in FIG. 1 and FIG. 3C. It will be recognized that the foregoing drive mechanisms are illustrative and non-limiting. Using the teachings provided herein a number of drive mechanisms can be integrated into SOCs.

In certain embodiments the sparse orthogonal collimators comprise one or more encoders to identify the location and/or movement of leaves comprising the collimators. Suitable encoders include, but are not limited to laser encoders (e.g., based on a displacement interferometer), optical encoders (e.g., utilizing a finely graduated scale and a compact optoelectronic readhead that converts motion relative to the scale into position data), magnetic encoders, capacitance/resistance encoders, and the like. Numerous high precision encoders are commercially available, e.g., from Renishaw Inc., Illinois.

In various embodiments, the collimator comprises 2 leaves per bank, or 4 leaves per bank, or 8 leaves per bank the last providing a maximum of 32 leaves per collimator. As explained herein a novel fluence map optimization method based on wavelet decomposition is described herein and used for IMRT with a sparse orthogonal collimator as described herein. In particular, an innovative algorithm was used to simplify the fluence maps with minimal and predictable dose quality compromise and Haar wavelet decomposition was utilized to convert the simplified fluence maps to patches that can be achieved using the SOC while maintaining high dosimetric quality. Compared to the conventional MLC using 120 leaved, similar level of intensity modulation can be achieved using 32 or fewer leaves in SOC. The SOC will be less expensive to make and maintain. It will achieve both high resolution and large field coverage. It is also feasible to make SOC for applications that are highly limited in space but higher resolution modulation is desired such as the small animal irradiation and robotically mounted linacs.

In certain embodiments the sparse orthogonal collimators (SOCs) described herein are effective to provide a treatment comparable to or better than that obtained with a multi-leaf collimator (MLC). In certain embodiments the dose to the planning target volume (PTV) obtained with the SOC is no less than 80%, or no less than 90%, or no less than about 95%, or no less than about 100% than the PTV obtained with an MLC and no greater than the OAR dosage, no more than about 2% greater than the OAR dosage, or no more than about 5% greater, or no more than about 10% greater OAR dosage than that obtained with an MLC.

In certain embodiments the sparse orthogonal collimators are incorporated into a treatment system for delivering radiation therapy to a subject. In certain embodiments the treatment system comprises a sparse orthogonal collimator as described herein and a radiotherapy device comprising the sparse orthogonal collimator disposed to control the field size and shape of emitted radiation, and a controller configured to adjust the position of the leaves comprising the sparse orthogonal collimator. In certain embodiments, the controller controls only the leaf position/movement in the collimator. In certain embodiments the controller, additionally controls one or more of the radiotherapy device gantry position, table position, beam time, beam intensity, and the like. In certain embodiments the radiotherapy device produces electron or photon beams. In certain embodiments radiotherapy device produces electron, neutron, proton, x-ray, or gamma radiation. In certain embodiments the radiotherapy device comprises a linear accelerator (linac) configured to provide X-rays. In certain embodiments the radiotherapy device is configured to operate in a coplanar beam orientation. In certain embodiments the radiotherapy device is configured to operate in a non-coplanar beam orientation.

Fluence Map Optimization for Sparse Orthogonal Collimators.

In certain embodiments methods of performing fluence optimization to optimize dose distribution using a sparse orthogonal collimator as described herein are provided. In certain embodiments Haar-based fluence optimization (HFO) is performed to optimize the fluence maps in the Haar wavelet domain, producing fluence maps that can be directly converted into a set of deliverable rectangular apertures. In order to optimize the dose distribution and minimize the number of apertures used, the overall objective can be formulated to incorporate an L2 penalty reflecting the difference between the prescription and the projected doses, and an L1 sparsity regularization term to encourage a low number of non-zero Haar wavelet coefficients. The optimization problem was solved using the Chambolle-Pock algorithm, a first-order primal-dual algorithm. These methods are described in detail in Example 1.

More particularly, in certain embodiments a method of generating a radiation treatment plan using a radiotherapy device comprising a sparse orthogonal collimator is provided where the method comprises providing a fluence maps for said radiation plan; and generating using a computer a time sequence of sparse orthogonal collimator leaf settings from the fluence maps, where the generating comprises:

representing a desired fluence map using discrete Haar wavelet coefficients; and optimizing Haar fluence using a direct aperture regularization approach centered on the dose domain optimization wherein sparsity is used to limit total number of Haar coefficients and thus total number of apertures while maintaining dosimetric quality; and generating and writing instruction files to implement said time sequence of sparse orthogonal collimator leaf settings to a tangible medium that can be executed by a radiotherapy device.

In certain embodiments as described in the Example, representing a desired fluence map can involve representing a fluence map, $f_{mat}$, using discrete Haar wavelet coefficients, $\alpha_c$, such that:

$$H_c^T \alpha_c H_c = f_{mat}, \quad (1)$$

where $H_c$ is the classical Haar transform matrix, but changing the differential Haar transform, $H_c$, to a scaling function, which is a modified Haar transform, $H_m$, that uses a coefficient set, $\alpha_m$ where for a $2^n \times 2^n$ fluence matrix, the coefficient matrix $\alpha_m$ has dimensions $(2^{n+1}-1) \times (2^{n+1}-1)$, and $H_m$ has dimensions $(2^{n+1}-1) \times 2^n$.

In certain embodiments the optimizing comprises:

$$\text{minimize } \tfrac{1}{2} \| W(AH_v \alpha_v - d_0) \|_2^2 + \lambda \| \alpha_v \|_1$$

$$\text{subject to } \alpha_v \geq 0, \quad (4)$$

where $\alpha_v = \text{vec}(\alpha_m)$ is the optimization variable; $H_v$ is the Haar transform matrix for the coefficient vector; W is a weighting factor for the structures of interest; A is the fluence to dose transformation matrix; and $d_0$ is the desired dose. In certain embodiments $d_0$ is set to the prescription dose for the planning target volume (PTV) and zero for the organs at risk (OARs). In certain embodiments the fluence to dose transformation matrix is calculated using a convolution/superposition code using a 6 MV x-ray polyenergetic kernel although other kernels can be used. In certain embodiments, as illustrated in the Example herein, the optimization can be solved utilizing the Chambolle-Pock algorithm. In various embodiments the method includes aperture constraints during the optimization stage rather than after the optimization.

In certain embodiments the writing instruction files comprises writing one or more instruction files to a tangible medium selected from the group consisting of a magnetic medium, an optical medium, a PAL chip, and a static RAM chip. In certain embodiments the writing instruction files comprises writing one or more instruction files to a CD, a flash drive, a DVD, and a hard drive. In certain embodiments the instruction files contain a treatment plan comprising sparse orthogonal collimator leaf positions and optionally one or more of the following: machine gantry and couch positions, beam intensities, and/or imager positions at a given time or plan delivery point. In certain embodiments the treatment plan comprises couch positions and gantry angles for a non-coplanar beam treatment. In certain embodiments the treatment plan comprises couch positions and gantry angles for a coplanar beam treatment.

In various embodiments a radiation treatment planning system for preparing treatment planning information for carrying out radiation treatment is provided. In certain embodiments the radiation treatment planning system comprises an input unit with which an operator inputs at least a prescription dose and a treatment volume; a computational unit configured to generate a radiation treatment plan using a radiotherapy device comprising a sparse orthogonal collimator described herein, and said computational unit determines apertures for said sparse orthogonal collimator, and optionally determines treatment beams, machine, and table paths; and a display unit that displays the radiation treatment plan. In certain embodiments the computational unit of the treatment planning system is configured to perform a fluence map optimization for an SOC as described herein. In certain embodiments the system further comprises a 3D scanning system. In certain embodiments the computational unit is configured to receive a CAT scan from a CT scanner or a patient medical record. In certain embodiments the system is configured to output a treatment plan into a patient medical record.

EXAMPLES

The following examples are offered to illustrate, but not to limit the claimed invention.

Example 1

A Novel Software and Conceptual Design of the Hardware Platform for Intensity Modulated Radiation Therapy To deliver high quality intensity modulated radiotherapy (IMRT) using a novel generalized sparse orthogonal collimators (SOC), we introduce a novel direct aperture optimization (DAO) approach based on discrete Haar wavelet representation.

II. Materials & Methods

II.1. Sparse Orthogonal Collimators

One illustrative sparse orthogonal collimator (SOC) design consists of two orthogonally oriented collimator systems with N number of leaves in each collimator bank, where N is a small number. The term "sparse" was chosen in contrast to the "dense" leaf arrangement in a conventional MLC. The nature of Haar wavelets requires the ideal number of leaves to be a power of 2. For this study, we estimated the delivery efficiency of SOC having N=1, N=2, and N=4 leaves in each bank, shown in FIG. 4. Evidently, jaws-only is a special case of SOC when N=1. In theory, the intensity modulation resolution of SOC is determined by the leaf step size instead of the leaf width.

II.2. Modified Haar Wavelet Transform

Like jaws-only IMRT, the apertures deliverable by SOC are rectangular. We represent an arbitrary fluence map, $f_{mat}$, using discrete Haar wavelet coefficients, $\alpha_c$, such that:

$$H_c^T \alpha_c H_c = f_{mat}, \tag{1}$$

where $H_c$ is the classical Haar transform matrix.

The Haar representation was motivated by the fact that SOCs would generate only rectangular apertures, since the most common classic dyadic Haar wavelets, which follow a geometric sequence of ratio 2, have the advantage to compactly represent piecewise smooth images. However, the differential forms in the Haar wavelet does not enable for the direct translation of the Haar coefficient to a corresponding non-negative fluence rectangle. Based on this, we modified the basis, essentially changing the differential Haar transform, $H_c$, to a scaling function, which we term the modified Haar transform, $H_m$. (see, e.g., FIG. 5) This uses a different coefficient set, notated as $\alpha_m$. For a $2^n \times 2^n$ fluence matrix, the coefficient matrix $\alpha_m$ has dimensions $(2^{n+1}-1) \times (2^{n+1}-1)$, and $H_m$ has dimensions $(2^{n+1}-1) \times 2^n$. For example, if the fluence matrix is a 4×4 matrix then the classical Haar matrix $$H_c = \begin{bmatrix} 1 & 1 & 1 & 1 \\ 1 & 1 & -1 & -1 \\ 1 & -1 & 0 & 0 \\ 0 & 0 & 1 & -1 \end{bmatrix}$$

is replaced with $$H_m = \begin{bmatrix} 1 & 1 & 1 & 1 \\ 1 & 1 & 0 & 0 \\ 0 & 0 & 1 & 1 \\ 1 & 0 & 0 & 0 \\ 0 & 1 & 0 & 0 \\ 0 & 0 & 1 & 0 \\ 0 & 0 & 0 & 1 \end{bmatrix} \tag{2}$$

And $\alpha_m$ is a 7×7 matrix.

In order to prepare for optimization, the coefficient matrix $\alpha_m$ and fluence map $f_{mat}$ were vectorized, denoted as $\alpha_v$ and $f_v$ respectively. To handle the vectorized notation, a special transform matrix, $H_v$ that incorporates both the vertical and horizontal operations produced by $H_m^T$ and $H_m$, was created. An expression to relate these variables together $$H_v \alpha_v = f_v = vec(f_{mat}) = vec(H_m^T \alpha_m H_m), \tag{3}$$

where vec(X) is the vectorization operator.

II.3. Optimization Formulation and Chambolle-Pock Algorithm

The optimization based on Haar wavelets is as follows:

$$\text{minimize } \tfrac{1}{2}\|W(AH_v\alpha_v - d_0)\|_2^2 + \lambda\|\alpha_v\|_1 \quad (4)$$

$$\text{subject to } \alpha_v \geq 0,$$

Where $\alpha_v = \text{vec}(\alpha_m)$ is the optimization variable, H is the Haar transform matrix for the coefficient vector $\alpha_v$, W is a weighting factor for the structures of interest, A is the fluence to dose transformation matrix, and $d_0$ is the desired dose, which is set to the prescription dose for the PTV and zero for the OARs. The fluence to dose transformation matrix is calculated using a convolution/superposition code using a 6 MV x-ray polyenergetic kernel.

The L2-norm data fidelity term penalizes any deviations in the dose from $d_0$, and the L1-norm sparsity term encourages a low number of non-zero coefficients. The definition of norm, for some vector x of length n, is $$\|x\|_p = \sqrt[p]{\sum_{i=1}^{n}|x_i|^p}.$$

The number of non-zero coefficients is exactly equal to the number of fluence segments for delivery. The weighting parameter $\lambda$ is used to regulate the number of non-zero coefficients.

Constraining $\alpha_v$ to stay positive is possible since the Haar transform was modified such that the value of the coefficients equals the value of the fluence.

The optimization problem was solved utilizing the Chambolle-Pock algorithm, a first-order primal-dual algorithm (Chambolle and Pock (2011) *J. Math. Imag. Vision*, 40(1): 120-145), where equation 4 is rewritten into the form $$\text{minimize } F(K\alpha_v) + G(\alpha_v), \quad (5)$$

where $$K = \begin{bmatrix} WAH_v \\ I \end{bmatrix}.$$

F and G are convex, lower semi-continuous functions and, for our particular problem, are defined as $$F(K\alpha_v) = F\left(\begin{bmatrix} WAH_v \\ I \end{bmatrix} |\alpha_v|\right) = F\left(\begin{bmatrix} WAH_v\alpha_v \\ \alpha_v \end{bmatrix}\right) = f_1(WAH_v\alpha_v) + f_2(\alpha_v) \quad (6)$$

$$G(\alpha_v) = \begin{cases} 0 & \text{if } \alpha_v \geq 0 \\ \infty & \text{otherwise,} \end{cases} \text{where}$$

$$f_1(y_1) = \tfrac{1}{2}\|y_1 - Wd_0\|_2^2, \quad (7)$$

$$f_2(y_2) = \lambda\|y_2\|_1.$$

This formulation can be solved using the over-relaxed Chambolle-Pock algorithm presented by Condat (Condat (2013) *J. Optimization Theory and App.* 158(2): 460-479), which uses the iteration $$\bar{\alpha}_v^{n+1} = \text{prox}_{\tau G}(\alpha_v^n - \tau K^T z^n) \quad (8)$$
$$\bar{z}^{n+1} = \text{prox}_{\sigma F^*}(z^n + \sigma K(2\bar{\alpha}_v^{n+1} - \alpha_v^n))$$
$$\alpha_v^{n+1} = p\bar{\alpha}_v^{n+1} + (1-p)\alpha_v^n$$
$$z^{n+1} = p\bar{z}^{n+1} + (1-p)z^n,$$

where $$\text{prox}_{\sigma F^*}(\hat{z}) = \text{prox}_{\sigma F^*}\begin{pmatrix}\hat{z}_1 \\ \hat{z}_2\end{pmatrix} = \begin{bmatrix} \text{prox}_{\sigma f_1^*}(\hat{z}_1) \\ \text{prox}_{\sigma f_2^*}(\hat{z}_2) \end{bmatrix} \quad (9)$$

$$\text{prox}_{\sigma f_1^*}(\hat{z}_1) = \frac{\hat{z}_1 - \sigma W d_0}{1+\sigma}$$

$$\text{prox}_{\sigma f_2^*}(\hat{z}_2) = P_{\lambda B}(\hat{z}_2)$$

$$\text{prox}_{\tau G}(\widehat{\alpha_v}) = P_+(\widehat{\alpha_v}).$$

As a primal-dual algorithm, the Chambolle-Pock algorithm solves both the primal problem, shown as equation 5, and its corresponding dual problem simultaneously by the iteration shown in equation set 8. Here, z is a variable in the dual formulation and is optimized alongside the primal variable $\alpha_v$. The proximal mapping function or "prox operator" is defined as $$\text{prox}_{th}(x) = \underset{u}{\text{argmin}}\left(h(u) + \frac{1}{2t}\|u-x\|_2^2\right)$$

and $\text{prox}_{\sigma F^*}(\hat{z})$ are $\text{prox}_{\tau G}(\widehat{\alpha_v})$ simplified into simple low cost calculations shown in equation set 9. The over-relaxation parameter is $0<p<2$, and the algorithm is equivalent to the original Chambolle-Pock algorithm when p=1. The step sizes $\tau$ and $\sigma$ must satisfy the constraint $\tau\sigma\|K\|^2 \leq 1$ for guaranteed convergence, and, in our experiments, are chosen as to satisfy $\tau\sigma\|K\|^2=1$. The norm of K is computed using the power iteration method (Golub and Van Loan, *Matrix computations*, Fourth edition. ed. The Johns Hopkins University Press, Baltimore, 2013). Further details on this algorithm are described previously (Nguyen et al. (2015) *Med. Phys.*, 42(4): 1858-1870).

Due the convex nature of the optimization problem, the starting values $\alpha_v^0$ and $z^0$ can be set as anything within the boundary constraints. For this study, $\alpha_v^0=0$ and $z^0=0$.

II.4. Evaluation

II.4.A. Patient Studies

Seven previously treated patients consisting of 2 glioblastoma multiforme patients (GBM), 3 head & neck patients (H&N), including 2 SBRT patients and 1 conventional fractionated patient with 3 PTVs (H&N$_{3PTV}$), and 2 lung patients (LNG) were included in the study. The prescription doses and PTV volumes are shown in Table 1. The patients were first planned on the $4\pi$ radiotherapy platform to optimize both beam orientation and fluence maps using previously described column generation and pricing approach (Romeijn et al. (2003) *Phys. Med. Biol.* 48(21): 3521-3542; Romeijn et al. (2005) *SIAM Optimiz.* 15(3): 838-862). During optimization, a 5 cm ring structure was added around the PTV to penalize the dose spillage to normal tissue. The platform has been shown to achieve superior dosimetry to coplanar volumetric modulated arc therapy (VMAT) (Dong et al. (2013) *Int, J, Radiat, Oncol, Biol, Phys*, 86(3): 407-413; Dong et al. (2013) *Int. J. Radiat. Oncol. Biol. Phys.* 85(5): 1360-1366; Dong et al. (2014) *Pract. Radiat. Oncol.* 4(4): 254-260). As a result of the optimization, 20 non-coplanar beams were selected from a candidate pool of 1162 equally spaced non-coplanar beams for each patient.

TABLE 1

Prescription doses and PTV volumes for each of the six cases.

|  | Prescription Dose (Gy) | PTV Volume (cc) |
|---|---|---|
| GBM #1 | 25 | 6.23 |
| GBM #2 | 30 | 57.77 |
| H&N #1 | 40 | 23.76 |
| H&N #2 | 40 | 18.86 |
| Lung #1 | 50 | 138.75 |
| Lung #2 | 50 | 47.78 |
| H&N$_{3PTV}$ | 54.00 | 238.60 |
|  | 59.40 | 687.38 |
|  | 69.96 | 254.98 |

The dose distributions were compared after generating deliverable segments on the two different platforms: 1) the Haar fluence optimization (HFO) method and 2) the direct MLC segmentation (DMS) method.

For the HFO plans, the optimized fluences from the 4π radiotherapy plan were not used while adopting the optimized beam angles. Rectangular apertures as the Haar wavelet basis were calculated using Eq. (1) and the Chambolle-Pock algorithm. λ was varied until the average number of segments per beam for each case was roughly 15.

For the DMS method, the raw fluence from the 4π radiotherapy plan was stratified and an MLC segmentation algorithm was applied to calculate the deliverable MLC segments. The MLC segmentation algorithm was based on a reduction level method by Xia and Verhey (Xia and Verhey (1998) Med. Phys. 25(8): 1424-1434), described previously in detail (Nguyen et al. (2015)Med. Phys., 42(4): 1858-1870). The stratification step size was adjusted through a bisection algorithm so that the number of calculated MLC segments in DMS equaled to that of HFO, and the MLC segments were calculated to be deliverable along the direction of leaf motion without any collimator rotations.

For all of the cases except the H&N$_{3PTV}$ HFO plan, the beamlet resolution was 0.5 cm$^2$ and the dose matrix resolution was 0.25 cm$^3$. Due to computational complexities of the optimization, the H&N$_{3PTV}$ HFO plan was evaluated with a beamlet resolution of 1 cm$^2$ and dose matrix resolution of 0.5 cm$^3$.

All treatment plans were normalized such that the prescription dose was delivered to 95% of the PTV. As dosimetric endpoints for comparison, R50 and PTV homogeneity, D98, D99, and Dmax, as well as OAR mean and max doses, were evaluated. R50 is a measure of high dose spillage, and is defined as the 50% isodose volume divided by the PTV volume. Homogeneity is defined as $$\frac{D95}{D5},$$

and maximum close is gained from ICRU Report 83 (Prescribing, Recording, and Reporting Intensity-Modulated Photon-Beam Therapy (IMRT)) (Grégoire and Mackie (2011) Cancer/Radiothérapie, 15(6-7): 555-559), where Dmax is defined as D2, the dose to 2% of the structure's volume.

Aperture size, reported as number of bixels, is evaluated and compared between the HFO and DMS methods for all seven cases. A bixel is a basic square unit on an IMRT fluence map, and aperture continuity is defined as the four directly neighboring bixels. The HFO method, by design, is limited to 1 aperture per delivery segment, while the DMS method can have multiple apertures per segment.

II.4.B. Sparse Orthogonal Collimator Travel Time Estimation

In order to evaluate the potential delivery time for using SOCs with N=1, N=2 and N=4 leaves per bank, the delivery order of the segments must first be optimized. The problem was formulated as a modified form of the open traveling salesman problem (TSP), and then solved using a basic genetic algorithm, an open source MATLAB code provided by Kirk (J. Kirk, in MATLAB (2008)).

The general TSP attempts to find the shortest path through a set of points in space, traveling to each point only once. The open variation of the problem allows for the end point to be different than the start point, rather than forming a closed loop. As a genetic algorithm, the open source code solves the TSP by first generating random populations, which are different potential routes that visit all points exactly once. The genetic algorithm then groups the paths into random groups of 4. For each group, it takes the population with the shortest route, randomly selects 2 of the points along the route, and performs 3 types of mutations on the sub-route between the 2 points: 1) Swap: take the 2 points and swap their order along the sub-route 2) Flip: The sub-route existing between the 2 selected points is reversed 3) Slide: All points between and including the 2 selected points is shifted by 1, with the first point becoming the last point on the sub-route. These 3 mutations replace the 3 worst solutions of the group of 4. This is performed for every grouping and repeated for a set number of iterations, selecting a different random grouping of 4 each time. After a set number of iterations, an optimal or near-optimal solution is found.

For our problem, each rectangular segment can be defined as 4 numbers describing the location of the collimator edge. In a sense, each rectangular segment can be mathematically described as a 4-dimensional point. Subtracting two of these points tells us how far each collimator has to travel from one segment to another. The open source code by Kirk can solve the TSP in any number of dimensions by finding the Euclidean norm distance between two points. Since the limiting factor in travel time between two segments is defined by the one collimator leaf that has to travel the furthest, the code was modified such that instead of using the Euclidean distance between two points, it used the single largest distance a collimator leaf had to travel for calculation.

In this study, 100 populations and 10000 iterations were used in the genetic algorithm to solve the TSP.

Once the order of the segments was solved, the collimator travel time was calculated with an estimated jaw acceleration of 5 cm/s$^2$ and maximal speed of 2 cm/s, which is typical for a C-arm linac.

Figures 4, 5:
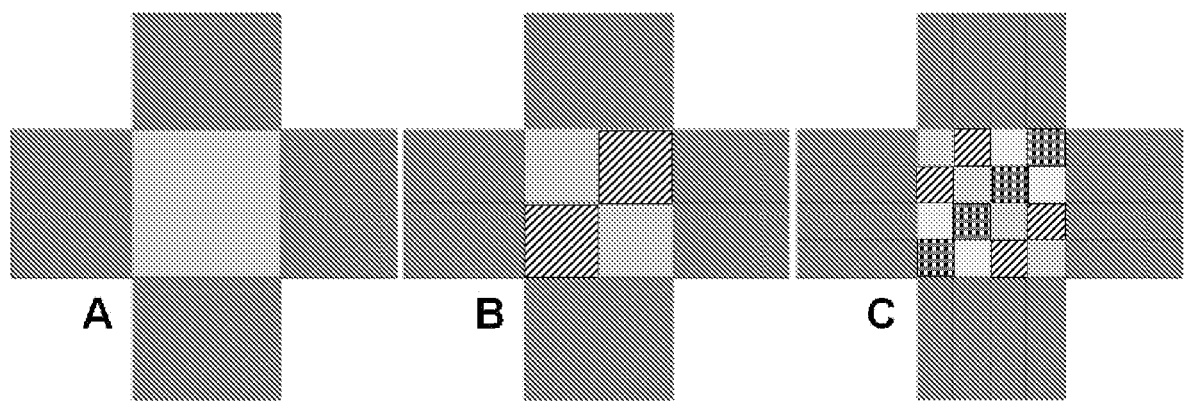
FIG. 4 shows a schematic of the SOC design with N=1 (A), N=2 (B), and N=4(C). Gray regions are the collimator leaves. Matching colored regions indicate areas where the fluence field can be delivered in parallel.
FIG. 5 shows a schematic of the classical Haar wavelet transform and a modified scaling function described herein.

The N=2 and N=4 SOC designs have color coded regions shown in FIG. 4 that can be delivered in parallel. To account for this, the segments are grouped into regions and an individual collimator travel time for each region is optimized and calculated separately. Between regions that can be simultaneously delivered, the longest travel time is recorded. When using SOC with N>1 to deliver a larger aperture, adjacent leaves move together as a single leaf.

The same aperture ordering scheme and time calculation, using the same jaw acceleration and maximal speed, was performed for DMS as well, with each aperture described as the location of every MLC location.

The total travel time for delivery and efficiency is evaluated for the 7 patients and compared between DMS and HFO with the N=1, N=2 and N=4 leaf collimator designs.

III. Results

III.1. Fluence Map Evaluation

Figure 6:
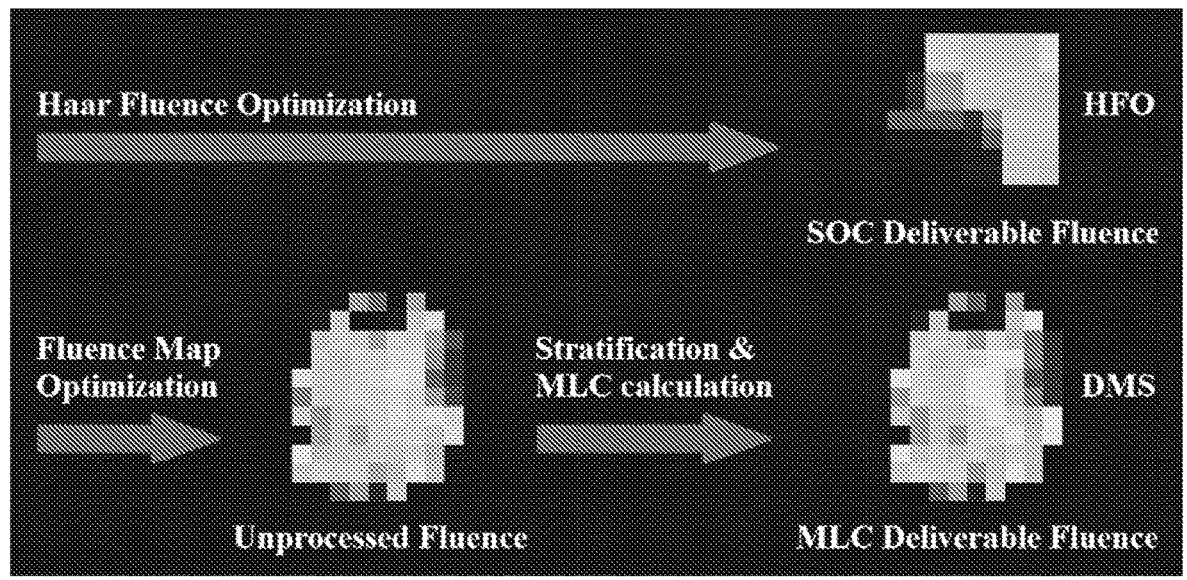
FIG. 6 shows a schematic of fluence maps produced by HFO and DMS method for the same beam angle.

FIG. 6 is a schematic of the fluences from the same beam angle and the MLC segmentation steps needed to create deliverable fluences. The DMS method requires extra post-optimization processing to stratify the fluence, which changes the optimized fluence and degrades the dosimetry. The HFO method, on the other hand, creates rectangles that can be delivered without any further processing of the fluence. Despite delivery from the same beam angle, the fluence patterns from the two methods are substantially different for most beam angles. This difference can be explained by the fact that HFO is a direct aperture regularization approach centered on the dose domain optimization. It utilizes the sparsity term to limit the total number of Haar coefficients, and therefore, limit the total number of apertures. HFO plans included the aperture constraints during the optimization stage while DMS incorporate the MLC constraints after the optimization.

Figure 7A:
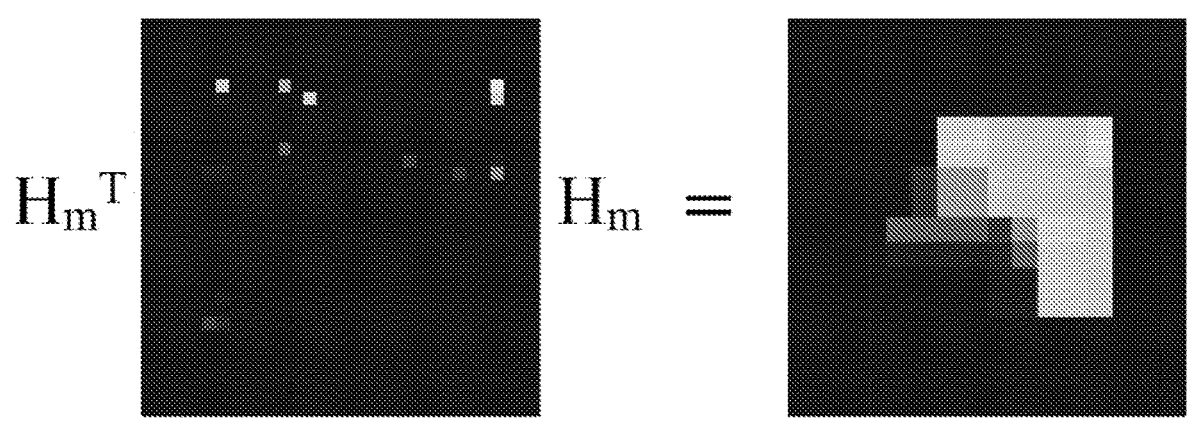
FIG. 7A illustrates the transform from Haar coefficients, our optimization variable, to the fluence domain.
Figure 7B:
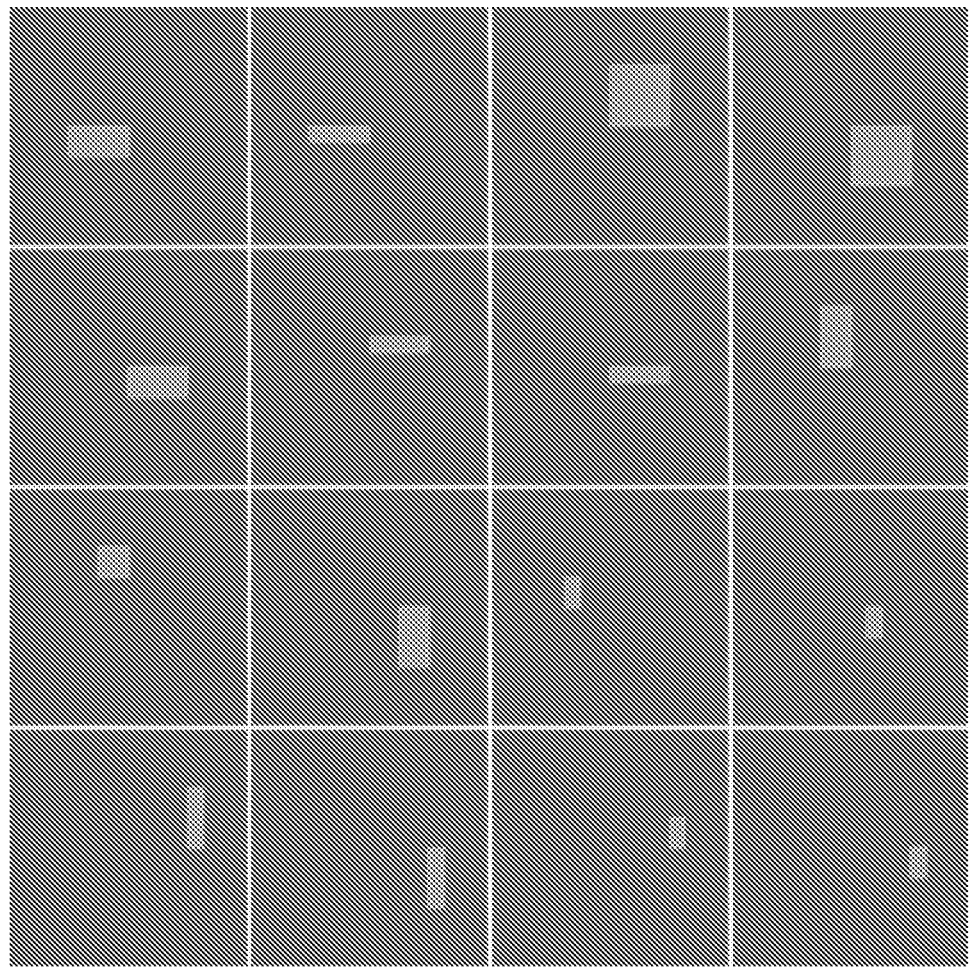
FIG. 7B shows the breakdown of the fluence map into its deliverable rectangles, which correspond directly to the Haar coefficients. On average, approximately 16 delivery segments per beam were used.
Figure 8A:
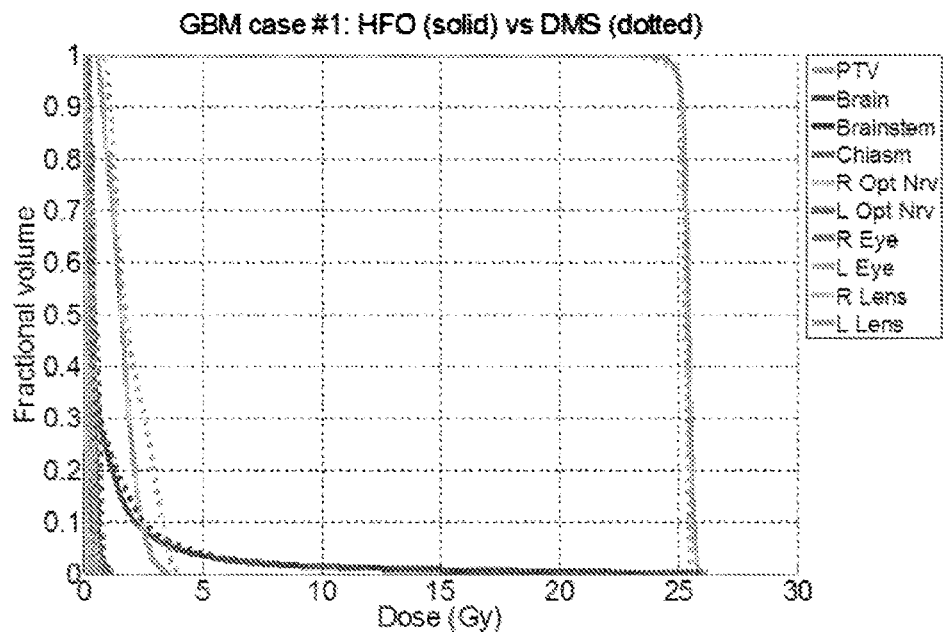
FIG. 8A shows DVH comparisons of a GBM case.
Figure 8B:
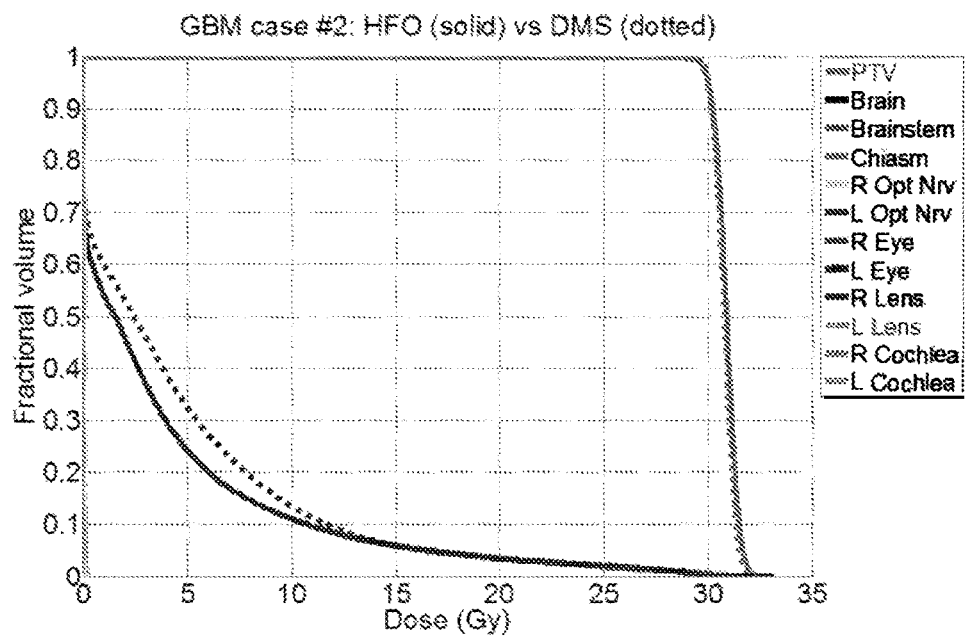
FIG. 8B shows DVH comparisons of another GBM case.
Figure 8C:
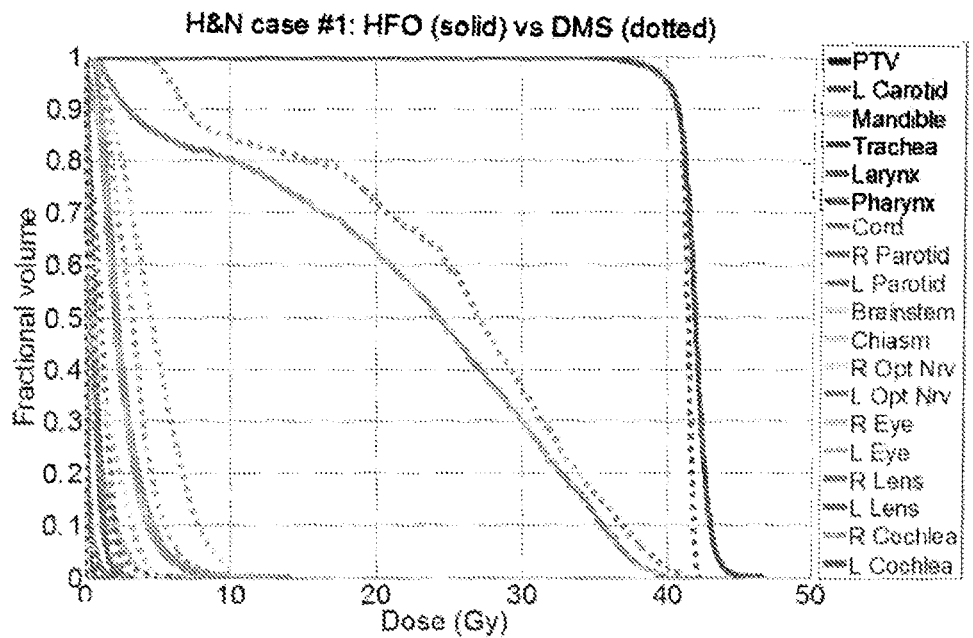
FIG. 8C shows DVH comparisons of a H&N case.
Figure 8D:
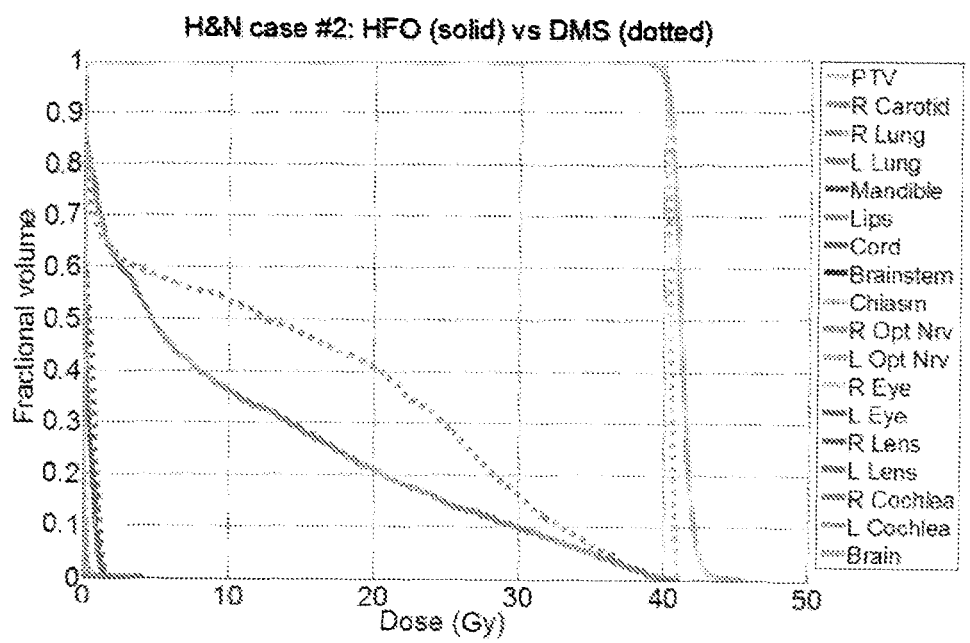
FIG. 8D shows DVH comparisons of another H&N case.
Figure 8E:
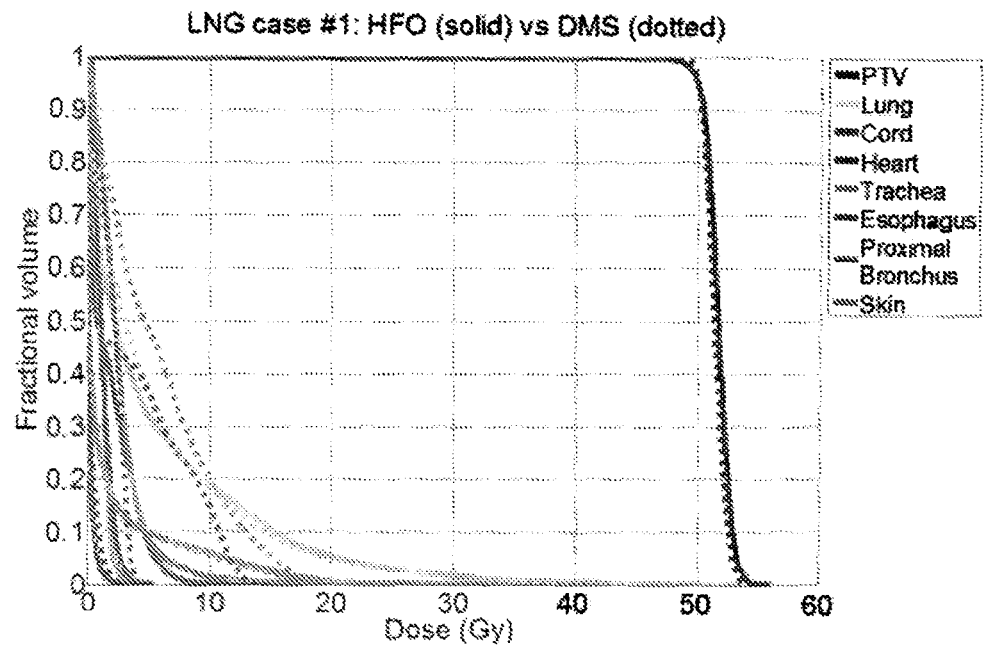
FIG. 8E shows DVH comparisons of a LNG case.
Figure 8F:
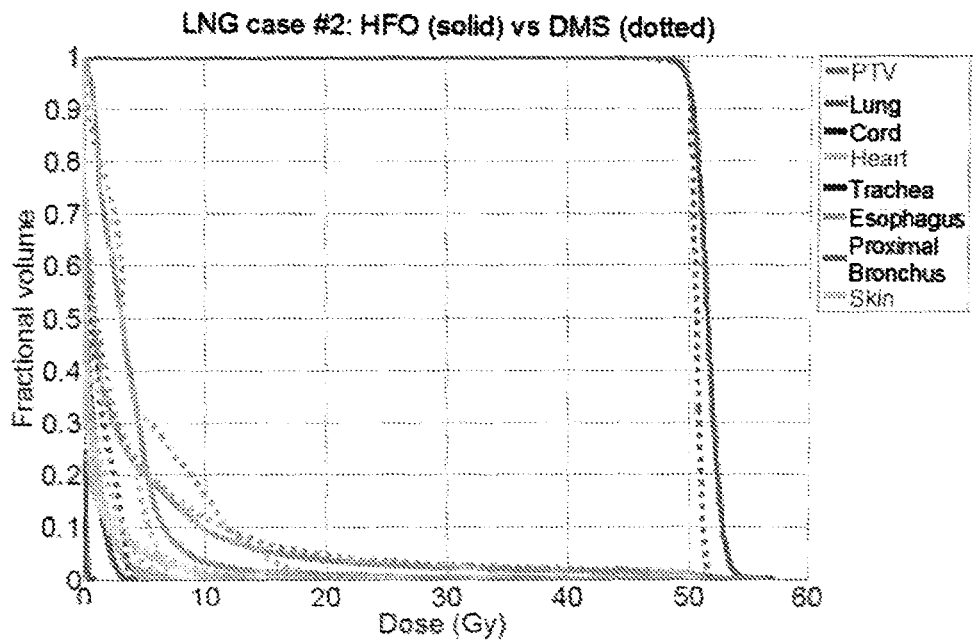
FIG. 8F shows DVH comparisons of another LNG case.
Figure 8G:
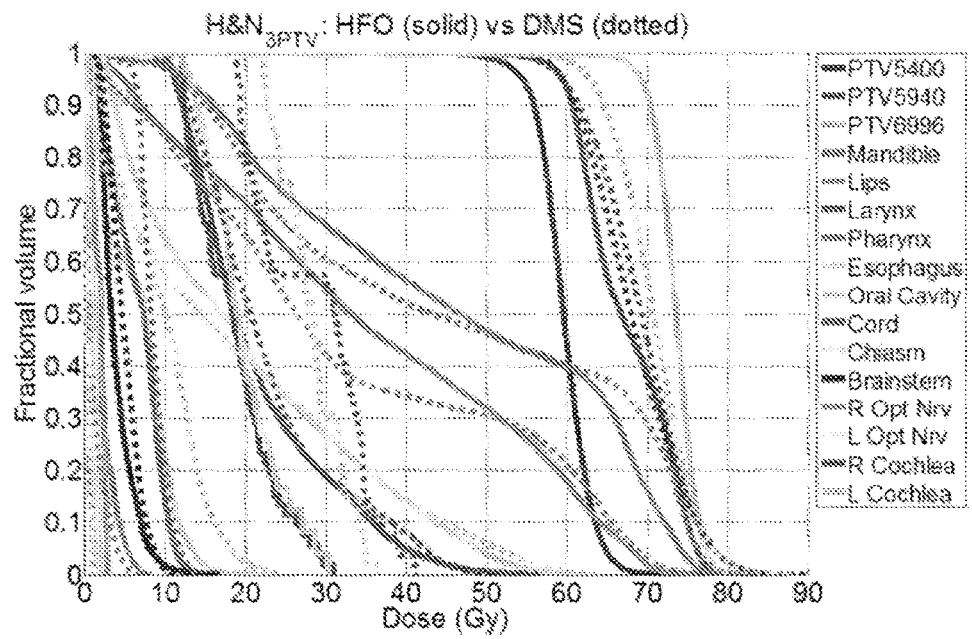
FIG. 8G shows DVH comparisons of a H&N$_{3PTV}$ case.

FIG. 7A illustrates the transform from Haar coefficients, our optimization variable, to the fluence domain, and 7B shows the breakdown of the fluence map into its deliverable rectangles, which correspond directly to the Haar coefficients. On average, approximately 16 delivery segments per beam were used.

III.2. Patient Results

Table 2 shows a comparison of PTV homogeneity, D98, D99, and Dmax as well as R50 and average number of delivery segments. Total average includes the PTVs from the 6 single target cases and the 59.4 Gy PTV from the H&N3PTV case. R50 from the H&N3PTV case is calculated based on the 59.4 Gy prescription dose and the total PTV volume contributed by all 3.

TABLE 2

Comparison of PTV homogeneity, D98, D99, and Dmax as well as R50 and average number of delivery segments.

| Patient Case | | Average number of segments per beam | PTV Statistics | | | | | R50 | |
|---|---|---|---|---|---|---|---|---|---|
| | | | Homogeneity | | D98 | D99 | Dmax | | |
| | | | HFO | DMS | HFO − DMS (Gy) | | | HFO | DMS |
| GBM #1 | | 13.90 | 0.973 | 0.981 | +0.135 | +0.246 | +0.265 | 4.009 | 4.015 |
| GBM #2 | | 14.65 | 0.948 | 0.952 | −0.084 | −0.168 | +0.202 | 2.833 | 2.818 |
| H&N #1 | | 16.00 | 0.924 | 0.955 | −0.019 | −0.022 | +1.884 | 3.805 | 4.384 |
| H&N #2 | | 14.60 | 0.943 | 0.980 | −0.186 | −0.392 | +1.961 | 3.729 | 4.377 |
| Lung #1 | | 17.70 | 0.939 | 0.946 | −0.409 | −0.791 | +0.520 | 3.555 | 3.225 |
| Lung #2 | | 14.45 | 0.941 | 0.974 | −0.204 | +0.024 | +2.005 | 3.055 | 3.824 |
| Average excluding H&N$_{3PTV}$ | | 15.22 | 0.945 | 0.965 | −0.128 | −0.184 | +1.140 | 3.498 | 3.774 |
| H&N$_{3PTV}$ | 54.00 | 23.40 | 0.841 | 0.760 | −5.696 | −6.566 | −14.339 | 2.954 | 2.681 |
| | 59.40 | | 0.781 | 0.760 | +0.490 | +0.137 | −3.322 | | |
| | 69.96 | | 0.897 | 0.803 | +6.846 | +6.936 | −2.198 | | |
| Total Average | | 16.39 | 0.921 | 0.935 | −0.040 | −0.138 | +0.502 | 3.420 | 3.618 |

Table 3 shows the largest and smallest values found for (HFO−DMS) dose differences for the Dmax and Dmean. The average value of the dose differences between OARs for each case is included. OARs that received 0 Gy in both the HFO and DMS cases are excluded in the evaluation.

TABLE 3

Largest and smallest values found for (HFO − DMS) dose differences for the Dmax and Dmean.

| Dose difference HFO − DMS (Gy) | Dmax | | | Dmean | | |
|---|---|---|---|---|---|---|
| | Largest value | Smallest value | Average value | Largest value | Smallest value | Average value |
| GBM #1 | +0.051 Chiasm | −0.726 R Opt Nrv | −0.193 | +0.001 L Opt Nrv | −0.420 R Opt Nrv | −0.131 |
| GBM #2 | +0.058 R Eye | −0.042 Chiasm | −0.011 | +0.003 R Eye | −0.011 L Opt Nrv | −0.004 |
| H&N #1 | +0.102 Brainstem | −3.073 Larynx | −0.959 | +0.018 L Cochlea | −2.938 L Carotid | −0.721 |
| H&N #2 | −0.011 Mandible | −0.173 Cord | −0.087 | +0.0001 Brainstem | −4.229 R Carotid | −0.634 |
| Lung #1 | +0.733 Trachea | −7.734 ProxBronch | −1.568 | +0.835 Trachea | −3.162 ProxBronch | −0.683 |

TABLE 3-continued

Largest and smallest values found for (HFO − DMS) dose differences for the Dmax and Dmean.

| Dose difference HFO − DMS (Gy) | Dmax | | | Dmean | | |
|---|---|---|---|---|---|---|
| | Largest value | Smallest value | Average value | Largest value | Smallest value | Average value |
| Lung #2 | +0.218 Trachea | −5.949 Lung | −2.362 | +0.039 Trachea | −1.220 ProxBronch | −0.527 |
| H&N$_{3PTV}$ | +1.662 R Opt Nrv | −11.250 R Cochlea | −1.900 | +2.634 Mandible | −9.843 R Cochlea | −1.365 |

FIGS. 8A-8G show the DVHs for all cases. The average difference (HFO−DMS) of D98, D99, and Dmax for the PTV between all cases, using only the 59.4 Gy PTV from the H&N$_{3PTV}$ case, was −0.093%, −0.273%, and +1.54%, respectively, as a percent of the prescription dose, indicating equivalent PTV coverage and slightly higher hot spots in the PTV HFO plans. Consequently, the PTV homogeneity, on average, is 0.014 lower with HFO than with DMS. On the other hand, HFO reduced R50 by 0.195, indicating a slightly improved high dose spillage to the body.

The H&N$_{3PTV}$ case had severe dose degradation in the DMS case after MLC segmentation. Before this post processing step, the plan was able to achieve a D95 of 55.3 Gy, 59.4 Gy, and 68.8 Gy for the 54 Gy PTV, 59.4 Gy PTV, and 69.96 Gy PTV, respectively. However, segmenting the large fluence maps into a relatively small number of deliverable segments caused the dose to degrade, and after normalization to the 59.4 Gy PTV, the D95 changed to 59.5 Gy, 59.4 Gy, and 62.9 Gy, respectively. The higher prescription level PTVs had large dose degradation, and the dose normalization caused overdosing to the 54 Gy PTV by an extra 5 Gy.

Figure 9:
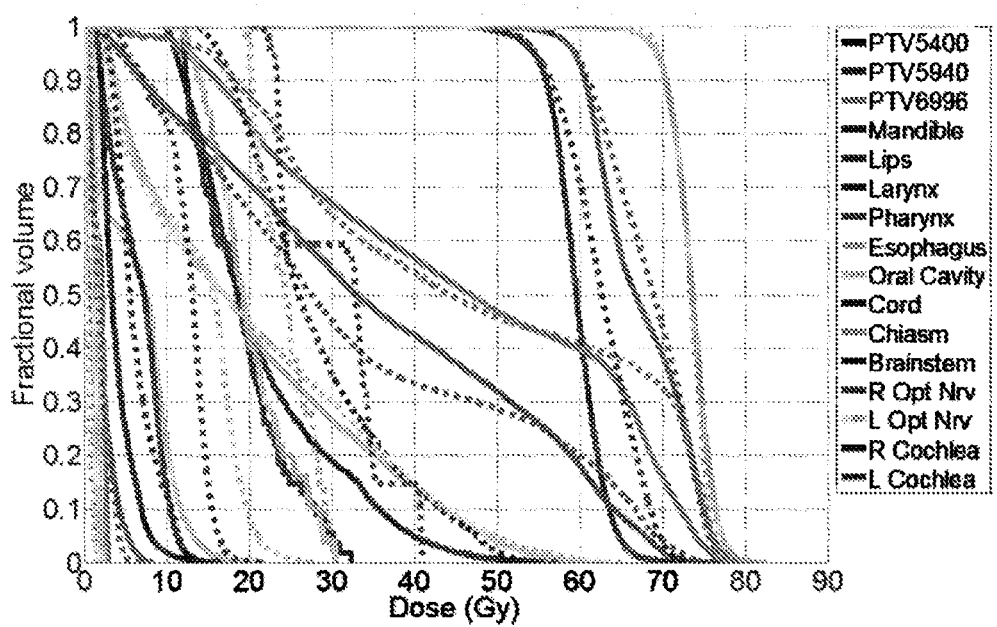
FIG. 9 shows DVH comparison between HFO and DDR methods for H&N$_{3PTV}$ case.

Due to the unacceptable dosimetry to the target volumes of the H&N$_{3PTV}$ caused by the DMS method, another plan, termed the dose domain regularized (DDR) plan (Nguyen et al. (2015)*Med. Phys.*, 42(4): 1858-1870), was included for comparison. DDR piecewise smooths the fluence using an anisotropic total variation regularization term while penalizing deviations from the optimal dose calculated from the $4\pi$ radiotherapy plan but before any post processing from the DMS plan. The DDR plan then underwent the same stratification and segmentation steps as the DMS plan. Even though the DDR plans and the DMS plans originated from the same exact $4\pi$ optimized plan, the DDR plan suffers much less from the stratification and segmentation steps, allowing for better dose coverage and homogeneity to the 69.96 Gy PTV than the HFO plan. A DVH comparison between HFO and DDR is shown in FIG. 9.

This average difference for maximum and mean dose for all OARs between all plans, excluding structures that received zero dose from both plans, are −2.27% and −1.38%, respectively, as a percent of the prescription dose, meaning that for typical radiotherapy plans that have a prescription dose ranging from 30 to 60 Gy, we can expect to spare from 0.681 Gy to 1.362 Gy of max dose and from 0.414 Gy to 0.828 Gy of mean dose to OARs.

Figure 10A:
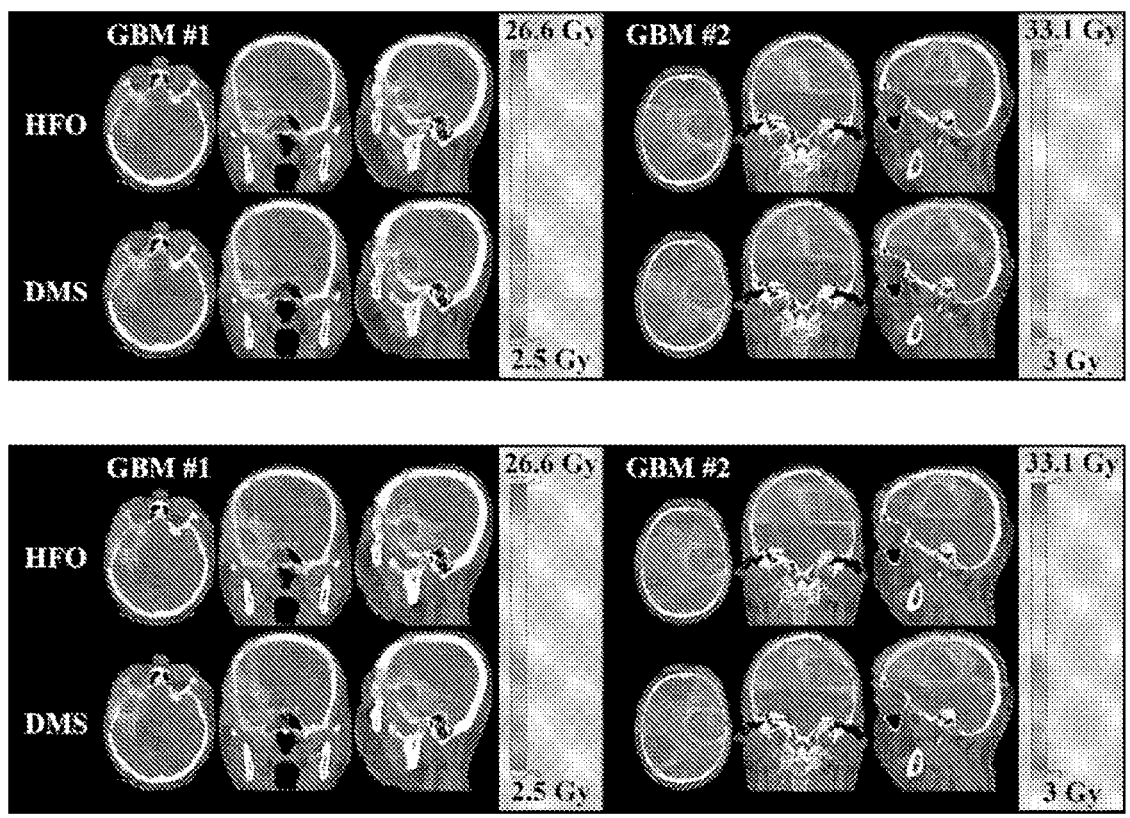
FIG. 10A shows dose color washes of GBM patients.
Figure 10B:
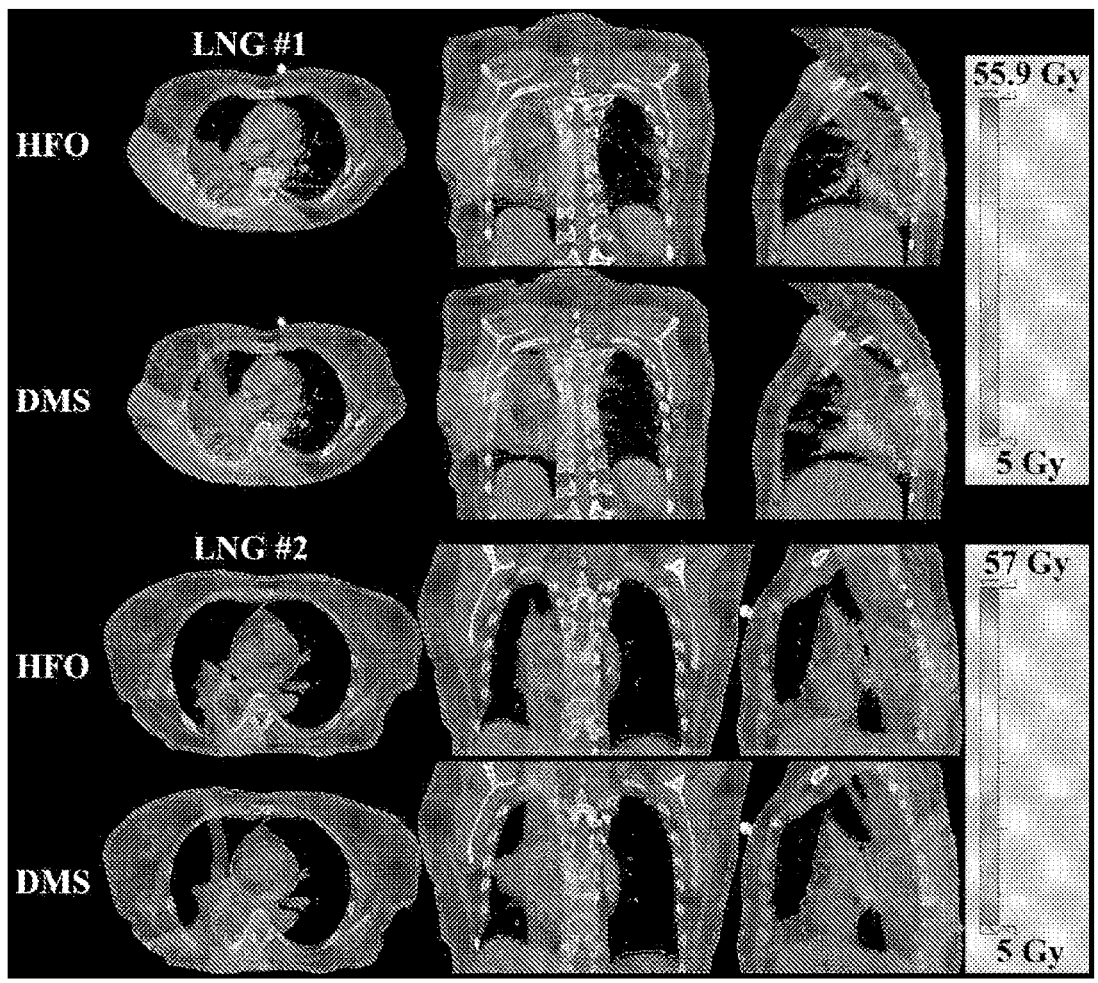
FIG. 10B shows dose color washes of LNG patient.
Figure 10C:
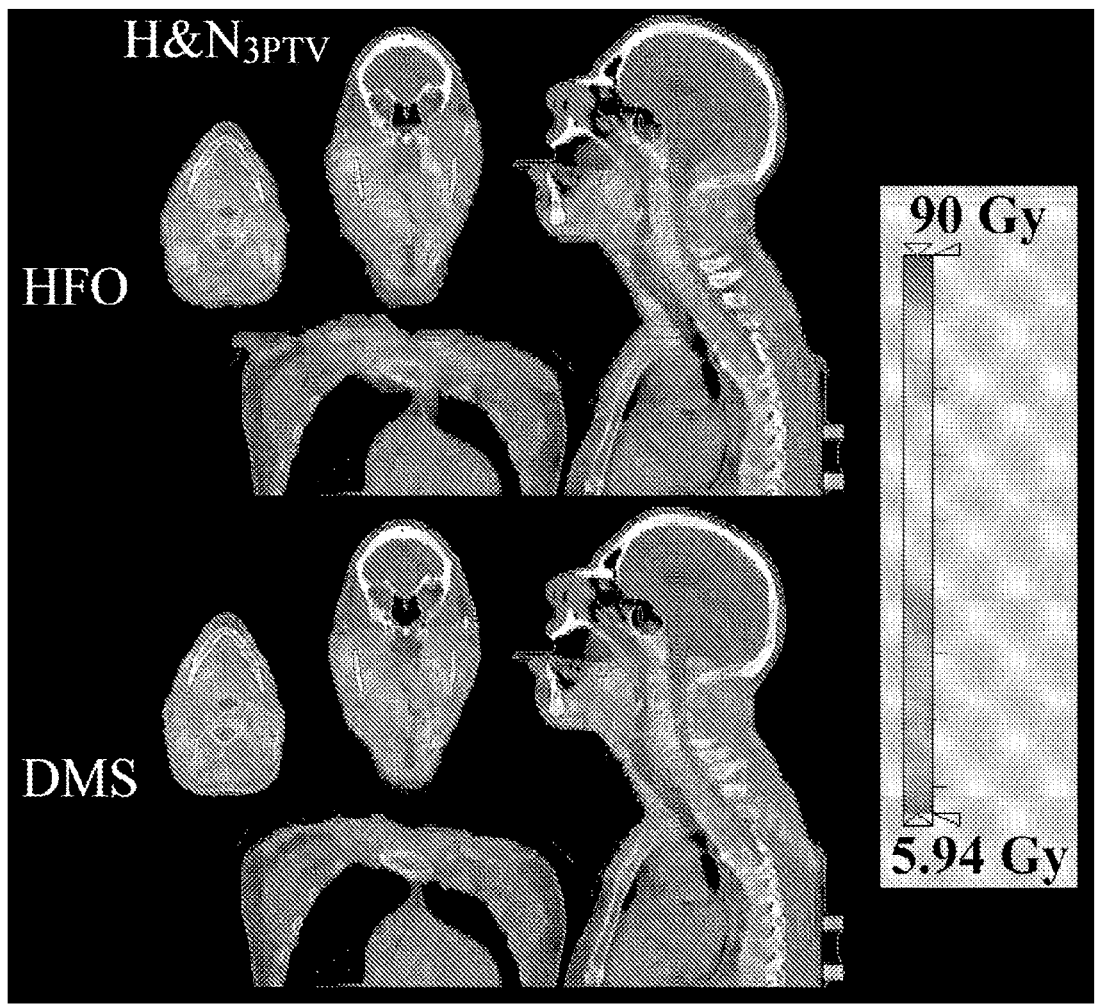
FIG. 10C shows dose color washes of H&N$_{3PTV}$ patients. The dose cutoff for viewing was chosen to be 10% of the prescription dose.

FIGS. 10A-10C show the dose color washes for the patient cases. Both methods achieved high dose conformality with comparable PTV coverage and slightly different normal organ dose distributions.

Figure 11:
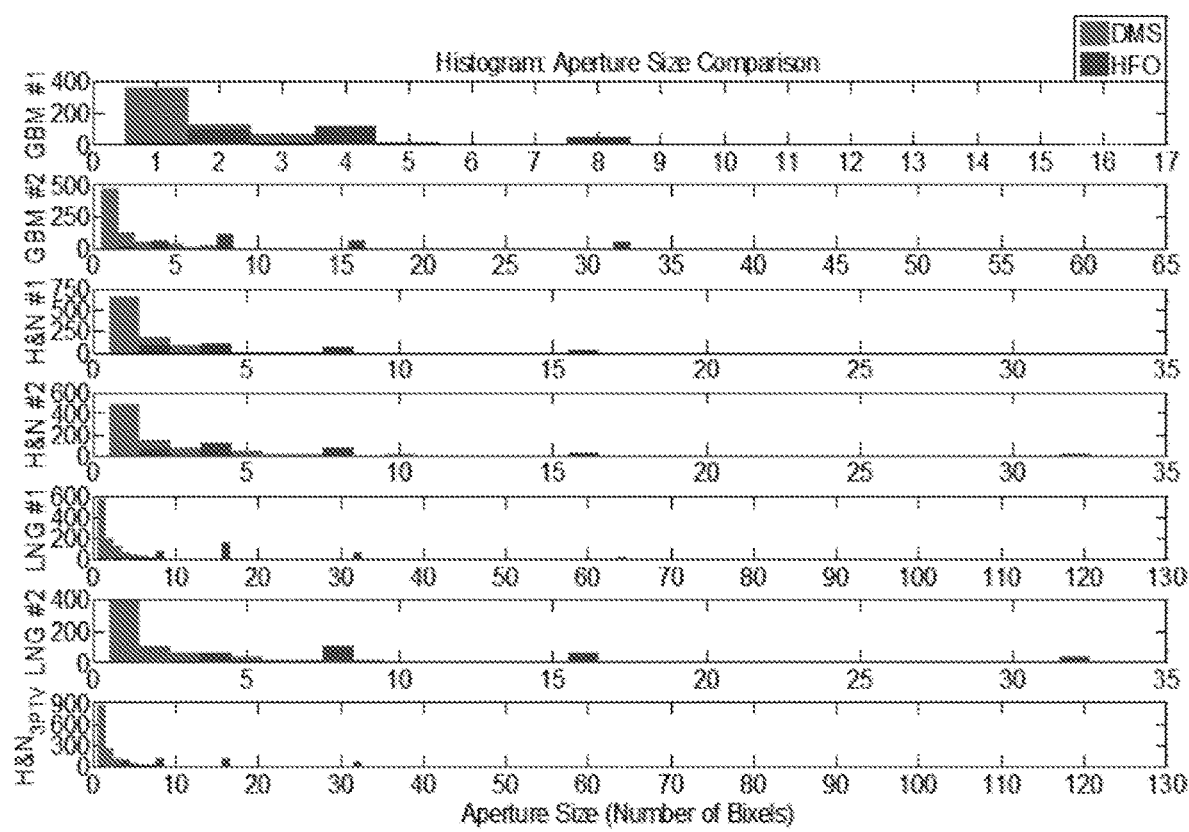
FIG. 11 shows histograms comparing the aperture sizes of the HFO and DMS method for each of the 7 cases.

Limited to one aperture per delivery segment, the HFO plan produced far fewer apertures than the DMS method, which had, on average, about 3 apertures per segment. The number of bixels that make up an aperture in the HFO method are limited as a power of 2, as shown on the histogram in FIG. 11. The mean aperture size for HFO is 4.4 times larger than the mean aperture size for DMS. The maximum aperture size is about 20 bixels larger using HFO comparing to DMS. The aperture statistics are shown in Table 4.

TABLE 4

Aperture statistics for the HFO and DMS methods for the 7 cases.

| | Total Number of Apertures | | Mean Aperture Size (Number of Bixels) | | Max Aperture Size (Number of Bixels) | |
|---|---|---|---|---|---|---|
| | HFO | DMS | HFO | DMS | HFO | DMS |
| GBM #1 | 278 | 629 | 4.20 | 1.90 | 16 | 10 |
| GBM #2 | 293 | 802 | 12.47 | 2.31 | 64 | 29 |
| H&N #1 | 320 | 1061 | 6.36 | 1.90 | 32 | 24 |
| H&N #2 | 292 | 888 | 6.90 | 2.44 | 32 | 24 |
| LNG #1 | 354 | 1165 | 19.97 | 3.08 | 128 | 78 |
| LNG #2 | 289 | 760 | 11.40 | 2.91 | 32 | 36 |
| H&N$_{3PTV}$ | 468 | 1556 | 16.32 | 3.10 | 128 | 88 |
| Average | 327.71 | 980.14 | 11.09 | 2.52 | 61.71 | 41.29 |

Figure 12A:
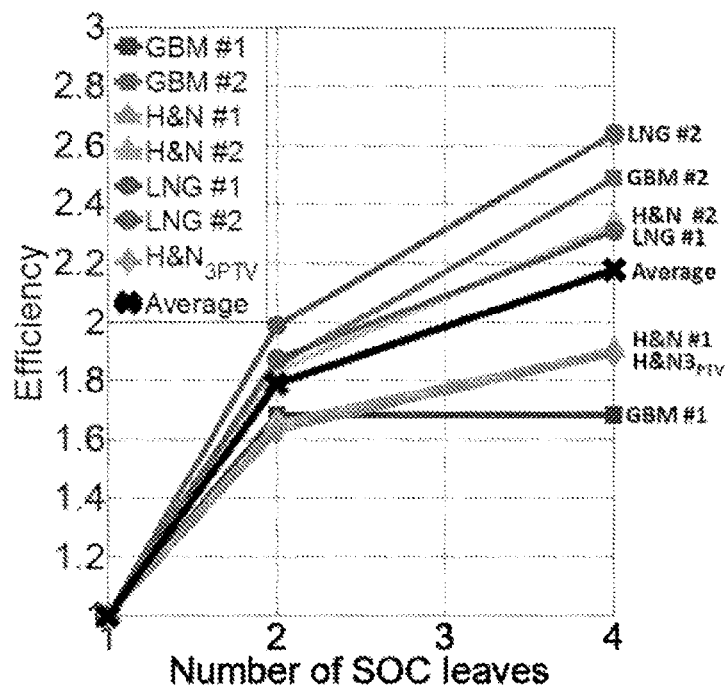
FIG. 12A shows a plot of Efficiency against the number of SOC leaves.
Figure 12B:
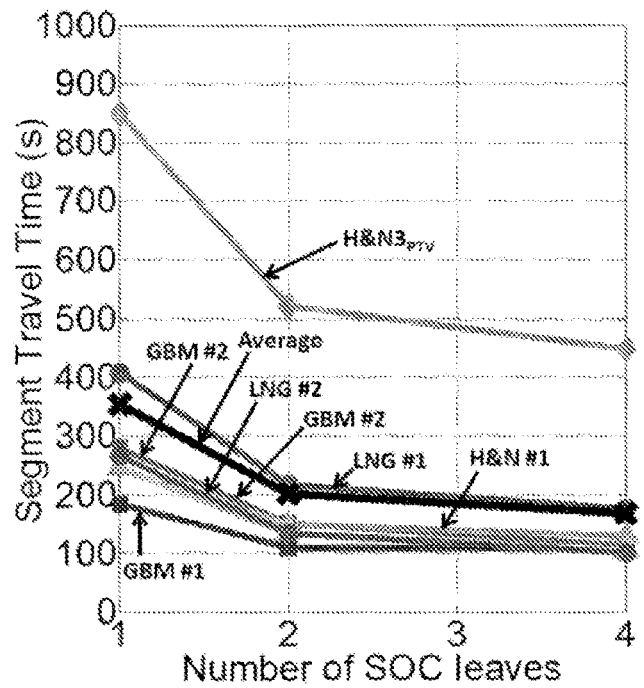
FIG. 12B shows a plot of Segment Travel Time against the number of SOC leaves.

FIG. 12A shows the total segment travel time for all 20 beams for each patient case, while FIG. 12B shows the efficiency for all 20 beams for each patient case. The average efficiency for the N=1, N=2 and N=4 leaf SOC designs is 1 (by definition), 1.78, and 2.18, respectively, and the average time is 354.23 s, 202.24 s, and 168.91 s, respectively. The largest gain in efficiency was observed when the SOC design was changed from N=1 to N=2. The N=4 design does further increases the efficiency, but a trend of diminishing returns is apparent. The average segment travel time between all patients for the DMS case was estimated to be 333.11 s, which is approximately 20 seconds faster delivery than the N=1 SOC design. The individual travel times are shown in Table 5. Overall, the total leaf travel times are consistent with 20 field step-and-shoot IMRT delivery.

TABLE 5

Comparison of the segment travel time between DMS and HFO with the various SOC designs.
Segment Travel Time Comparison (s)

|  | DMS | HFO N = 1 | HFO N = 2 | HFO N = 4 |
|---|---|---|---|---|
| GBM #1 | 210.79 | 184.54 | 109.54 | 109.54 |
| GBM #2 | 332.26 | 280.81 | 151.46 | 112.85 |
| H&N #1 | 268.81 | 245.75 | 148.40 | 129.16 |
| H&N #2 | 239.80 | 245.33 | 133.85 | 105.15 |
| LNG #1 | 354.34 | 407.08 | 217.31 | 176.27 |
| LNG #2 | 262.37 | 265.90 | 133.84 | 100.69 |
| H&N$_{3PTV}$ | 663.40 | 850.20 | 521.30 | 448.70 |
| Average | 333.11 | 354.23 | 202.24 | 168.91 |

DISCUSSION

In the study, we presented a novel method to generate rectangular apertures for SOC IMRT delivery. This method is based on regularization of the Haar wavelet coefficient in the dose domain to minimize the number of apertures while maintaining the dosimetric quality. Compared to the MLC-based plans, despite the remarkable simplification of fluence maps into deliverable rectangles, the direct aperture optimization nature allows HFO to stay competitive. Our study was based on a non-coplanar beam orientation optimization platform that we previously showed to be superior to coplanar arc plans. However, the same HFO method should apply to coplanar IMRT without modification.

Although the Chambolle-Pock algorithm is remarkably efficient in solving the dose domain optimization problem, the computational cost of HFO plans remains substantial, particularly for larger PTVs. The length and width of the fluence grid are discretized to be a power of 2 to work properly. For instance, using our beamlet size of 0.5 cm², any plan with a PTV larger than 4 cm but smaller than 8 cm in diameter must use a 16×16 fluence grid, even if it is just slightly larger than 4 cm. The H&N$_{3PTV}$ plan had the largest PTV dimension measuring approximately 20 cm. If HFO was performed using the regular beamlet size, this plan would have required a 64×64 fluence grid for each beam. Our modified Haar wavelet space then has a resolution of 127×127 pixels, making the optimizer solve 322580 variables simultaneously for all 20 beams. The inclusion of a dose domain transformation matrix, which contains tens of millions of non-zero entries, in the optimization further increases the computational complexity. The amount of data that must be handled simultaneously in the memory would exceed the available 512 GB RAM on our present workstation for larger PTVs and high dose calculation resolution. Therefore, the HFO method for the H&N$_{3PTV}$ plan was recalculated at half the dose matrix resolution and half of the beamlet resolution to achieve a reasonable cost optimization although superior dosimetric quality is expected had the higher dose resolution been used.

Jaws-only IMRT was initially developed as an alternative method to MLC based IMRT, which was costly and unreliable in its early stage. However, with the maturation of MLC technology, the need has considerably declined for general purpose IMRT on state of the art C-arm machines. The SOC IMRT, however, may be appealing in several aspects. First, even for N=4, the SOC system still has far fewer and thicker moving leaves than the conventional MLC allowing it to be further miniaturized to enable compact linac heads (Dong et al. (2014) Med. Phys. 41(4): 041709) and small animal irradiators. An effective way to reduce the linac head size is by moving the beam intensity modulator closer to the X-ray source. Moving the MLC closer to the X-ray source while maintaining the same intensity modulation resolution is increasingly difficult since a shorter source-to-collimator distance would require reduction of the already thin MLC leaf width, making fabrication more challenging, reducing mechanical reliability and increasing the interleaf leakage from the loss of the tongue and groove. In comparison, the resolution of SOC IMRT is not dependent on the leaf width, but rather on the motor accuracy capable of being in the micron range. For the same reason, the undesirable tradeoff between large field size and high resolution MLCs can be avoided with SOC. Third, as shown in the aperture size comparison, the SOC plan apertures are on average 4.4 times larger than those of the MLC plans. This would allow a significantly shorter beam-on time, reduced leakage dose and potentially improved IMRT QA results.

The dosimetric improvement was driven by the novel HFO algorithm. To overcome the other major deficiency of jaw-only IMRT, the SOC utilizing increasing number of leaves per bank can significantly improve delivery efficiency. The number of leaves in the SOC described herein is still far fewer than the typical number of leaves in a MLC, thus maintaining the ability to miniaturize and achieve a higher modulation resolution. Based on our estimation, increasing N beyond 4 may still increase the delivery efficiency but the returns start to diminish because although the same colored areas can be delivered in parallel, these areas are smaller and more fragmented with increasing N. Multiple leaves need to move in synchrony to deliver X-rays in the rest of the area, resulting in the diminished return for more leaves per bank. Considering the increasing mechanical complexity, an N=2-N=4 leaf/bank design may be an optimal balance between complexity and delivery efficiency.

In this study, the potential dosimetric advantages of using higher achievable resolution were not explored.

V. Conclusion

The IMRT problem was formulated into a direct aperture optimization problem minimizing the dose error while solving for the fluences in the Haar wavelet domain. This resulted in rectangular apertures that can be directly delivered with jaws only. The delivery efficiency may further be enhanced using modified sparse orthogonal collimators (SOC) utilizing 2-4 leaves per collimator bank. The potential gains from the greater resolution capabilities of jaws and SOCs have yet to be fully explored because of current computational limits in handling the number of discretized beamlets for Haar wavelet decomposition.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of generating a radiation treatment plan using a radiotherapy device comprising a sparse orthogonal collimator comprising a first bank of individually longitudinally movable elongate leaves, and a second bank of individually longitudinally movable elongate leaves the second bank being disposed in an opposed relationship to the first bank, a third bank of individually longitudinally movable elongate leaves, and a fourth bank of individually longitudinally movable elongate leaves the fourth bank being disposed in an opposed relationship to said third bank, and said first bank and said second bank being oriented orthogonal to said third bank and fourth bank, and said first bank, second bank, third bank, and fourth bank each individually contain from two to four leaves, said method comprising:

providing a fluence map for said radiation treatment plan; and generating using a computer a time sequence of sparse orthogonal collimator leaf settings from said fluence maps, wherein said generating comprises:

representing a desired fluence map using discrete Haar wavelet coefficients; and optimizing Haar fluence using a direct aperture regularization approach centered on dose domain optimization wherein sparsity is used to limit total number of Haar coefficients and thus total number of apertures while maintaining dosimetric quality; and generating and writing instruction files to implement said time sequence of sparse orthogonal collimator leaf settings to a tangible medium accessible for execution by the radiotherapy device.

2. The method of claim 1, wherein said representing a desired fluence map comprises representing a fluence map, fmat using discrete Haar wavelet coefficients, $\alpha c$, such that:

$$H_c^T \alpha_c H_c = f_{mat}, \quad (1)$$

where $H_c$ is the classical Haar transform matrix, but changing the differential Haar transform, $H_c$, to a scaling function, which is a modified Haar transform, $H_m$ that uses a coefficient set, $\alpha_m$ where for a $2^n \times 2^n$ fluence matrix, the coefficient matrix $\alpha_m$ has dimensions $(2^n+1-1) \times (2^n+1-1)$, and $H^m$ has dimensions $(2^n+1-1) \times 2^n$.

3. The method according to claim 1, wherein said optimizing comprises:

$$\text{minimize } \tfrac{1}{2}\|W(AH_v \alpha_v - d_0)\|_2^2 + \lambda \|\alpha_v\|_1$$

$$\text{subject to } \alpha_v \geq 0, \quad (4)$$

where $\alpha_v = \text{vec}(\alpha_m)$ is the optimization variable;

$H_v$ is the Haar transform matrix for the coefficient vector;

W is a weighting factor for the structures of interest;

A is the fluence to dose transformation matrix; and $d_0$ is the desired dose.

4. The method of claim 3, wherein $d_0$ is set to the prescription dose for the planning target volume (PTV) and zero for the organs at risk (OARs).

5. The method of claim 3, wherein the fluence to dose transformation matrix is calculated using a convolution/superposition code using a 6 MV x-ray polyenergetic kernel.

6. The method of claim 3, wherein said instruction files contain a treatment plan comprising sparse orthogonal collimator leaf positions and optionally one or more of the following: machine gantry and couch positions, beam intensities, imager positions at a given time or plan delivery point.

7. The method of claim 6, wherein said treatment plan comprises couch positions and gantry angles for a non-coplanar beam treatment.

* * * * *

UNITED STATES PATENT AND TRADEMARK OFFICE
CERTIFICATE OF CORRECTION

PATENT NO. : 10,987,523 B2  
APPLICATION NO. : 15/770489  
DATED : April 27, 2021  
INVENTOR(S) : Ke Sheng et al.

Page 1 of 1

It is certified that error appears in the above-identified patent and that said Letters Patent is hereby corrected as shown below:

In the Specification

Column 10, Line 40, "patient" should be --patients--.

Column 17, Line 10, "H" should be --$H_v$--.

Column 18, Line 57, "SIAM Optimiz" should be --SIAM J. Optimiz--.

Column 19, Line 55, "close is gained" should be --dose is defined--.

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*